(12) United States Patent
Shmeis et al.

(10) Patent No.: US 10,517,832 B2
(45) Date of Patent: *Dec. 31, 2019

(54) TAMPER RESISTANT PHARMACEUTICAL FORMULATIONS

(71) Applicant: Purdue Pharma L.P., Stamford, CT (US)

(72) Inventors: Rama Abu Shmeis, Branchburg, NJ (US); Sheetal R. Muley, Piscataway, NJ (US); Xiaohong Shen, Livingston, NJ (US); Zhixin Zong, Franklin Park, NJ (US)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/234,732

(22) Filed: Dec. 28, 2018

(65) Prior Publication Data

US 2019/0167597 A1 Jun. 6, 2019

(51) Int. Cl.
*A61K 9/20* (2006.01)
*A61K 9/28* (2006.01)
(Continued)

(52) U.S. Cl.
CPC .......... *A61K 9/2081* (2013.01); *A61K 9/1652* (2013.01); *A61K 9/2013* (2013.01); *A61K 9/2018* (2013.01); *A61K 9/2027* (2013.01); *A61K 9/2031* (2013.01); *A61K 9/2054* (2013.01); *A61K 9/2095* (2013.01); *A61K 9/2846* (2013.01); *A61K 9/4808* (2013.01); *A61K 9/501* (2013.01); *A61K 9/5015* (2013.01); *A61K 9/5026* (2013.01); *A61K 9/5047* (2013.01); *A61K 9/5073* (2013.01);
(Continued)

(58) Field of Classification Search
CPC .. A61K 9/2081; A61K 9/2085; A61K 9/5084; A61K 9/5095
See application file for complete search history.

(56) References Cited

U.S. PATENT DOCUMENTS 3,065,143 A 11/1962 Christenson et al.
3,096,248 A 7/1963 Rudzki
(Continued)

FOREIGN PATENT DOCUMENTS

CA 2569743 12/2005
CA 2594373 8/2006
(Continued)

OTHER PUBLICATIONS

Ansel, Howard C., et al., Pharmaceutical Dosage Forms and Drug Delivery Systems, 7th Edition, 1999, pp. 1-2, 23-163, 179-243, 397-449, 552-562, Lippincott Williams & Wilkins, United States.
(Continued)

*Primary Examiner* — Carlos A Azpuru
(74) *Attorney, Agent, or Firm* — Lowenstein Sandler LLP

(57) ABSTRACT

Disclosed in certain embodiments is a solid oral dosage form comprising a plurality of particles, each particle comprising (i) a core comprising an active agent susceptible to abuse and an internal adhesion promoter, wherein the cores are (i) dispersed in a matrix comprising a controlled release material or (ii) coated with a controlled release material. The dosage form can also include an alcohol resistant material.

19 Claims, 26 Drawing Sheets

(51) Int. Cl.
*A61K 31/485*     (2006.01)
*A61K 9/48*       (2006.01)
*A61K 9/50*       (2006.01)
*A61K 47/10*      (2017.01)
*A61K 47/32*      (2006.01)
*A61K 47/38*      (2006.01)
*A61K 9/16*       (2006.01)

(52) U.S. Cl.
CPC .......... *A61K 9/5084* (2013.01); *A61K 9/5089* (2013.01); *A61K 31/485* (2013.01); *A61K 47/10* (2013.01); *A61K 47/32* (2013.01); *A61K 47/38* (2013.01)

(56) References Cited

U.S. PATENT DOCUMENTS

| | | |
|---|---|---|
| 3,133,132 A | 5/1964 | Loeb et al. |
| 3,173,876 A | 3/1965 | Zobrist et al. |
| 3,260,646 A | 7/1966 | Paulsen |
| 3,276,586 A | 10/1966 | Rosaen |
| 3,400,197 A | 9/1968 | Lippman |
| 3,541,005 A | 11/1970 | Strathmann et al. |
| 3,541,006 A | 11/1970 | Bixler et al. |
| 3,546,876 A | 12/1970 | Fokker et al. |
| 3,845,770 A | 11/1974 | Theeuwes et al. |
| 3,879,555 A | 4/1975 | Pachter et al. |
| 3,916,889 A | 11/1975 | Russell |
| 3,965,256 A | 6/1976 | Leslie |
| 3,980,766 A | 9/1976 | Shaw et al. |
| 4,063,064 A | 12/1977 | Saunders et al. |
| 4,070,494 A | 1/1978 | Hollmeister et al. |
| 4,088,864 A | 5/1978 | Theeuwes et al. |
| 4,160,020 A | 7/1979 | Ayer et al. |
| 4,175,119 A | 11/1979 | Porter |
| 4,200,098 A | 4/1980 | Ayer et al. |
| 4,235,870 A | 11/1980 | Leslie |
| 4,285,987 A | 8/1981 | Ayer et al. |
| 4,293,539 A | 10/1981 | Ludwig et al. |
| 4,366,310 A | 12/1982 | Leslie |
| 4,385,057 A | 5/1983 | Bjork et al. |
| 4,389,393 A | 6/1983 | Schor et al. |
| 4,424,205 A | 1/1984 | LaHann et al. |
| 4,443,428 A | 4/1984 | Oshlack et al. |
| 4,457,933 A | 7/1984 | Gordon et al. |
| 4,459,278 A | 7/1984 | Porter |
| 4,588,580 A | 5/1986 | Gale et al. |
| 4,599,342 A | 7/1986 | LaHann |
| 4,610,870 A | 9/1986 | Jain et al. |
| 4,612,008 A | 9/1986 | Wong et al. |
| 4,629,623 A | 12/1986 | Balazs et al. |
| 4,666,705 A | 5/1987 | DeCrosta et al. |
| 4,764,378 A | 8/1988 | Keith et al. |
| 4,765,989 A | 8/1988 | Wong et al. |
| 4,769,372 A | 9/1988 | Kreek |
| 4,785,000 A | 11/1988 | Kreek et al. |
| 4,806,341 A | 2/1989 | Chien et al. |
| 4,812,446 A | 3/1989 | Brand |
| 4,834,984 A | 5/1989 | Goldie et al. |
| 4,844,909 A | 7/1989 | Goldie et al. |
| 4,861,598 A | 8/1989 | Oshlack |
| 4,957,681 A | 9/1990 | Klimesch et al. |
| 4,970,075 A | 11/1990 | Oshlack |
| 4,990,341 A | 2/1991 | Goldie et al. |
| 4,992,277 A | 2/1991 | Sangekar et al. |
| 5,026,556 A | 6/1991 | Drust et al. |
| 5,059,600 A | 10/1991 | Gawin et al. |
| 5,069,909 A | 12/1991 | Sharma et al. |
| 5,111,942 A | 5/1992 | Bernardin |
| 5,113,585 A | 5/1992 | Rogers et al. |
| 5,114,942 A | 5/1992 | Gawin et al. |
| 5,130,311 A | 7/1992 | Guillaumet et al. |
| 5,149,538 A | 9/1992 | Granger et al. |
| 5,169,645 A | 12/1992 | Shukla et al. |
| 5,202,128 A | 4/1993 | Morella et al. |
| 5,215,758 A | 6/1993 | Krishnamurthy |
| 5,225,199 A | 7/1993 | Hidaka et al. |
| 5,232,685 A | 8/1993 | Speck et al. |
| 5,232,934 A | 8/1993 | Downs |
| 5,240,711 A | 8/1993 | Hille et al. |
| 5,266,331 A | 11/1993 | Oshlack et al. |
| 5,273,758 A | 12/1993 | Royce |
| 5,273,760 A | 12/1993 | Oshlack et al. |
| 5,286,493 A | 2/1994 | Oshlack et al. |
| 5,290,816 A | 3/1994 | Blumberg |
| 5,300,302 A | 4/1994 | Tachon et al. |
| 5,321,012 A | 6/1994 | Mayer et al. |
| 5,324,351 A | 6/1994 | Oshlack et al. |
| 5,330,766 A | 7/1994 | Morella et al. |
| 5,356,467 A | 10/1994 | Oshlack et al. |
| 5,376,705 A | 12/1994 | Leys et al. |
| 5,378,474 A | 1/1995 | Morella et al. |
| 5,399,351 A | 3/1995 | Leschiner et al. |
| 5,403,868 A | 4/1995 | Reid et al. |
| 5,409,944 A | 4/1995 | Black et al. |
| 5,411,745 A | 5/1995 | Oshlack et al. |
| 5,422,123 A | 6/1995 | Conte et al. |
| 5,425,950 A | 6/1995 | Dandiker et al. |
| 5,436,265 A | 7/1995 | Black et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,489,439 A | 2/1996 | Bola |
| 5,500,227 A | 3/1996 | Oshlack et al. |
| 5,502,058 A | 3/1996 | Mayer et al. |
| 5,505,959 A | 4/1996 | Tachon et al. |
| 5,508,042 A | 4/1996 | Oshlack et al. |
| 5,508,043 A | 4/1996 | Krishnamurthy |
| 5,510,368 A | 4/1996 | Lau et al. |
| 5,514,680 A | 5/1996 | Weber et al. |
| 5,521,213 A | 5/1996 | Prasit et al. |
| 5,536,507 A | 7/1996 | Abramowitz et al. |
| 5,536,752 A | 7/1996 | Ducharme et al. |
| 5,549,912 A | 8/1996 | Oshlack et al. |
| 5,549,913 A | 8/1996 | Colombo et al. |
| 5,550,142 A | 8/1996 | Ducharme et al. |
| 5,552,422 A | 9/1996 | Gauthier et al. |
| 5,556,838 A | 9/1996 | Mayer et al. |
| 5,567,439 A | 10/1996 | Myers et al. |
| 5,580,578 A | 12/1996 | Oshlack et al. |
| 5,593,694 A | 1/1997 | Hayashida et al. |
| 5,593,695 A | 1/1997 | Merrill et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,639,476 A | 6/1997 | Oshlack et al. |
| 5,639,789 A | 6/1997 | Lau et al. |
| 5,654,005 A | 8/1997 | Chen et al. |
| 5,656,295 A | 8/1997 | Oshlack et al. |
| 5,667,805 A | 9/1997 | Merrill et al. |
| 5,672,360 A | 9/1997 | Sackler et al. |
| 5,676,972 A | 10/1997 | Galiatsatos et al. |
| 5,679,650 A | 10/1997 | Fukunaga et al. |
| 5,681,585 A | 10/1997 | Oshlack et al. |
| 5,695,781 A | 12/1997 | Zhang et al. |
| 5,702,725 A | 12/1997 | Merrill et al. |
| 5,730,716 A | 3/1998 | Beck et al. |
| 5,741,524 A | 4/1998 | Staniforth et al. |
| 5,762,963 A | 6/1998 | Byas-Smith |
| 5,766,623 A | 6/1998 | Aryes et al. |
| 5,788,987 A | 8/1998 | Busetti et al. |
| 5,811,126 A | 9/1998 | Krishnamurthy |
| 5,811,388 A | 9/1998 | Friend et al. |
| 5,814,336 A | 9/1998 | Kelm et al. |
| 5,837,379 A | 11/1998 | Chen et al. |
| 5,843,480 A | 12/1998 | Miller et al. |
| 5,849,240 A | 12/1998 | Miller et al. |
| 5,866,164 A | 2/1999 | Kuczynski et al. |
| 5,879,705 A | 3/1999 | Heafield et al. |
| 5,891,471 A | 4/1999 | Miller et al. |
| 5,891,919 A | 4/1999 | Blum et al. |
| 5,914,131 A | 6/1999 | Miller et al. |

(56) References Cited

U.S. PATENT DOCUMENTS

| | | |
|---|---|---|
| 5,945,125 A | 8/1999 | Kin |
| 5,948,787 A | 9/1999 | Merrill et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,024,982 A | 2/2000 | Oshlack |
| 6,103,261 A | 8/2000 | Chasin et al. |
| 6,120,751 A | 9/2000 | Unger |
| 6,124,282 A | 9/2000 | Sellers et al. |
| 6,126,969 A | 10/2000 | Shah et al. |
| 6,136,864 A | 10/2000 | Nichols et al. |
| 6,143,322 A | 11/2000 | Sackler et al. |
| 6,153,621 A | 11/2000 | Hamann |
| 6,162,467 A | 12/2000 | Miller et al. |
| 6,210,712 B1 | 4/2001 | Edgren et al. |
| 6,210,714 B1 | 4/2001 | Oshlack et al. |
| 6,223,075 B1 | 4/2001 | Beck et al. |
| 6,228,863 B1 | 5/2001 | Palermo et al. |
| 6,245,357 B1 | 6/2001 | Edgren et al. |
| 6,251,430 B1 | 6/2001 | Zhang et al. |
| 6,277,398 B1 | 8/2001 | Caruso |
| 6,294,194 B1 | 9/2001 | Horhota et al. |
| 6,309,668 B1 | 10/2001 | Bastin et al. |
| 6,348,469 B1 | 2/2002 | Seth |
| 6,352,721 B1 | 3/2002 | Faour |
| 6,365,185 B1 | 4/2002 | Ritschel et al. |
| 6,372,254 B1 | 4/2002 | Ting et al. |
| 6,375,957 B1 | 4/2002 | Kaiko et al. |
| 6,403,056 B1 | 6/2002 | Unger |
| 6,419,954 B1 | 7/2002 | Chu |
| 6,419,960 B1 | 7/2002 | Krishnamurthy et al. |
| 6,436,441 B1 | 8/2002 | Sako et al. |
| 6,440,464 B1 | 8/2002 | Hsia et al. |
| 6,455,537 B1 | 9/2002 | Cooper |
| 6,485,748 B1 | 11/2002 | Chen et al. |
| 6,488,963 B1 | 12/2002 | McGinity |
| 6,491,949 B2 | 12/2002 | Faour et al. |
| 6,559,159 B2 | 5/2003 | Carroll et al. |
| 6,572,885 B2 | 6/2003 | Oshlack et al. |
| 6,593,367 B1 | 7/2003 | Dewey et al. |
| 6,627,635 B2 | 9/2003 | Palermo et al. |
| 6,696,088 B2 | 2/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,761,895 B2 | 7/2004 | Sawada et al. |
| 6,808,720 B2 | 10/2004 | Unger |
| 6,955,821 B2 | 10/2005 | Davis et al. |
| 6,987,082 B2 | 1/2006 | Tijsma et al. |
| 6,995,169 B2 | 2/2006 | Chapleo et al. |
| RE39,239 E | 8/2006 | Busetti et al. |
| 7,141,250 B2 * | 11/2006 | Oshlack .............. A61K 9/2013 424/490 |
| 7,144,587 B2 | 12/2006 | Oshlack et al. |
| 7,157,103 B2 | 1/2007 | Sackler |
| 7,201,920 B2 | 4/2007 | Kumar et al. |
| 7,276,250 B2 | 10/2007 | Baichwal et al. |
| 7,332,182 B2 | 2/2008 | Sackler |
| 7,399,488 B2 | 7/2008 | Hirsch et al. |
| 7,510,726 B2 | 3/2009 | Kumar et al. |
| 7,718,194 B2 | 5/2010 | Chenevier et al. |
| 7,727,557 B2 | 6/2010 | Sackler |
| 7,776,314 B2 | 8/2010 | Bartholomaus |
| 7,842,307 B2 | 11/2010 | Oshlack et al. |
| 7,842,311 B2 | 11/2010 | Oshlack et al. |
| 7,943,174 B2 | 5/2011 | Oshlack et al. |
| 7,981,439 B2 | 7/2011 | Kumar et al. |
| 8,017,148 B2 | 9/2011 | Sackler |
| 8,075,872 B2 | 12/2011 | Arkenau-Maric et al. |
| 8,101,630 B2 | 1/2012 | Kumar et al. |
| 8,114,383 B2 | 2/2012 | Bartholomaus |
| 8,114,384 B2 | 2/2012 | Arkenau et al. |
| 8,143,267 B2 | 3/2012 | Burch et al. |
| 8,192,722 B2 | 6/2012 | Arkenau-Maric et al. |
| 8,193,209 B2 | 6/2012 | Burch et al. |
| 8,293,277 B2 | 10/2012 | Swanson et al. |
| 8,309,060 B2 | 11/2012 | Bartholomaus et al. |
| 8,323,692 B2 | 12/2012 | Frisbee |
| 8,337,888 B2 | 12/2012 | Wright et al. |
| 8,389,007 B2 | 3/2013 | Wright et al. |
| 8,394,408 B2 | 3/2013 | Han et al. |
| 8,409,616 B2 | 4/2013 | Kumar et al. |
| 8,524,275 B2 | 9/2013 | Oshlack et al. |
| 8,529,948 B1 | 9/2013 | Wright et al. |
| 8,551,520 B2 | 10/2013 | Oshlack et al. |
| 8,609,143 B2 | 12/2013 | Fischer et al. |
| 8,609,683 B2 | 12/2013 | Wright et al. |
| 8,617,600 B2 | 12/2013 | Bhatt et al. |
| 8,637,540 B2 | 1/2014 | Kumar et al. |
| 8,647,667 B2 | 2/2014 | Oshlack et al. |
| 8,652,497 B2 | 2/2014 | Sackler |
| 8,652,515 B2 | 2/2014 | Sackler |
| 8,652,529 B2 | 2/2014 | Guimberteau et al. |
| 8,871,265 B2 | 10/2014 | Wright et al. |
| 8,999,961 B2 | 4/2015 | Wright et al. |
| 9,034,376 B2 | 5/2015 | Wright et al. |
| 9,040,084 B2 | 5/2015 | Wright et al. |
| 9,044,435 B2 | 6/2015 | Wright et al. |
| 9,060,976 B2 | 6/2015 | Wright et al. |
| 9,233,073 B2 | 1/2016 | Sackler |
| 9,616,030 B2 | 4/2017 | Shmeis et al. |
| 2001/0031278 A1 | 10/2001 | Oshlack et al. |
| 2002/0028240 A1 | 3/2002 | Sawada et al. |
| 2002/0187192 A1 | 12/2002 | Joshi et al. |
| 2003/0004177 A1 | 1/2003 | Kao et al. |
| 2003/0021841 A1 | 1/2003 | Matharu et al. |
| 2003/0026838 A1 | 2/2003 | Farrell |
| 2003/0035839 A1 | 2/2003 | Hirsh et al. |
| 2003/0059471 A1 | 3/2003 | Compton et al. |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0082230 A1 | 5/2003 | Baichwal |
| 2003/0091625 A1 | 5/2003 | Hariharan et al. |
| 2003/0092724 A1 | 5/2003 | Kao et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0126428 A1 | 7/2003 | Liu et al. |
| 2003/0170181 A1 | 9/2003 | Midha |
| 2003/0190362 A1 | 10/2003 | Sackler et al. |
| 2003/0206954 A1 | 11/2003 | Lerner et al. |
| 2003/0232081 A1 | 12/2003 | Doshi et al. |
| 2004/0010000 A1 | 1/2004 | Ayer et al. |
| 2004/0047907 A1 | 3/2004 | Oshlack et al. |
| 2004/0110781 A1 | 6/2004 | Harmon et al. |
| 2004/0126428 A1 | 7/2004 | Hughes et al. |
| 2004/0131552 A1 | 7/2004 | Boehm |
| 2004/0151791 A1 | 8/2004 | Mayo-Alvarez et al. |
| 2004/0202717 A1 | 10/2004 | Mehtha |
| 2004/0224020 A1 | 11/2004 | Schoenhard |
| 2004/0228802 A1 | 11/2004 | Chang et al. |
| 2004/0241234 A1 | 12/2004 | Vikov |
| 2004/0253310 A1 | 12/2004 | Fischer et al. |
| 2004/0258749 A1 | 12/2004 | Guldner et al. |
| 2004/0266807 A1 | 12/2004 | Oshlack et al. |
| 2005/0020613 A1 | 1/2005 | Boehm et al. |
| 2005/0031546 A1 | 2/2005 | Bartholomaus et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0112201 A1 | 5/2005 | Baichwal et al. |
| 2005/0118267 A1 | 6/2005 | Baichwal et al. |
| 2005/0158382 A1 | 7/2005 | Cruz et al. |
| 2005/0163717 A1 | 7/2005 | Anderson et al. |
| 2005/0186139 A1 | 8/2005 | Bartholomaeus et al. |
| 2005/0214223 A1 | 9/2005 | Bartholomaeus et al. |
| 2005/0232987 A1 | 10/2005 | Srinivasan et al. |

(56) References Cited

U.S. PATENT DOCUMENTS

| | | |
|---|---|---|
| 2005/0236741 A1 | 10/2005 | Arkenau et al. |
| 2005/0276853 A1 | 12/2005 | Baichwal et al. |
| 2006/0002860 A1 | 1/2006 | Bartholomaus et al. |
| 2006/0018837 A1 | 1/2006 | Preston et al. |
| 2006/0039864 A1 | 2/2006 | Bartholomaus et al. |
| 2006/0165790 A1 | 7/2006 | Walden et al. |
| 2006/0188447 A1 | 8/2006 | Arkenau-Maric et al. |
| 2006/0193782 A1 | 8/2006 | Bartholomaus et al. |
| 2006/0210631 A1 | 9/2006 | Patel et al. |
| 2006/0240107 A1 | 10/2006 | Lenaerts |
| 2006/0251721 A1 | 11/2006 | Cruz et al. |
| 2007/0003616 A1 | 1/2007 | Arkenau-Maric et al. |
| 2007/0003617 A1 | 1/2007 | Fischer et al. |
| 2007/0020335 A1 | 1/2007 | Chen et al. |
| 2007/0110807 A1 | 5/2007 | Vergnault et al. |
| 2007/0166234 A1 | 7/2007 | Kumar et al. |
| 2007/0183980 A1 | 8/2007 | Arkenau-Maric et al. |
| 2007/0224129 A1 | 9/2007 | Guimberteau et al. |
| 2007/0264327 A1 | 11/2007 | Kumar et al. |
| 2008/0026060 A1 | 1/2008 | Zerbe et al. |
| 2008/0057123 A1 | 3/2008 | Grenier et al. |
| 2008/0063725 A1 | 3/2008 | Guimbertau et al. |
| 2008/0090892 A1 | 4/2008 | Casteel et al. |
| 2008/0095843 A1 | 4/2008 | Nutalapati et al. |
| 2008/0107732 A1 | 5/2008 | Dharmadhikari et al. |
| 2008/0147044 A1 | 6/2008 | Palmer et al. |
| 2008/0175908 A1 | 7/2008 | Liu et al. |
| 2008/0176955 A1 | 7/2008 | Heck et al. |
| 2008/0187581 A1 | 8/2008 | Gore et al. |
| 2008/0254123 A1 | 10/2008 | Fischer et al. |
| 2008/0260815 A1 | 10/2008 | Hayes et al. |
| 2008/0260824 A1 | 10/2008 | Nangia et al. |
| 2008/0311191 A1 | 12/2008 | Nangia et al. |
| 2009/0011019 A1 | 1/2009 | Jahagirdar et al. |
| 2009/0022798 A1 | 1/2009 | Rosenberg et al. |
| 2009/0081290 A1 | 3/2009 | McKenna et al. |
| 2009/0169587 A1 | 7/2009 | Baichwal et al. |
| 2009/0215808 A1 | 8/2009 | Yum et al. |
| 2009/0232885 A1 | 9/2009 | Venkatesh et al. |
| 2009/0269393 A1 | 10/2009 | Kashid et al. |
| 2010/0015222 A1 | 1/2010 | Han et al. |
| 2010/0015223 A1 | 1/2010 | Cailly-Dufestel et al. |
| 2010/0221293 A1 | 9/2010 | Cruz et al. |
| 2011/0020451 A1 | 1/2011 | Bartholomaus et al. |
| 2011/0223244 A1 | 9/2011 | Liversidge et al. |
| 2011/0262532 A1 | 10/2011 | Oshlack et al. |
| 2012/0164220 A1 | 6/2012 | Huang |
| 2012/0244216 A1 | 9/2012 | Shah et al. |
| 2013/0209525 A1 | 8/2013 | Cruz et al. |
| 2013/0217716 A1 | 8/2013 | Wright et al. |
| 2013/0245055 A1 | 9/2013 | Wright et al. |
| 2014/0056979 A1 | 2/2014 | Huang |
| 2014/0213606 A1 | 7/2014 | Wright et al. |
| 2014/0371257 A1 | 12/2014 | Wright et al. |
| 2015/0005331 A1 | 1/2015 | Wright et al. |
| 2015/0031718 A1 | 1/2015 | Wright et al. |
| 2015/0140083 A1 | 5/2015 | Wright et al. |
| 2015/0147391 A1 | 5/2015 | Wright et al. |
| 2015/0148319 A1 | 5/2015 | Wright et al. |
| 2015/0182628 A1 | 7/2015 | Wright et al. |

FOREIGN PATENT DOCUMENTS

| | | |
|---|---|---|
| CA | 2746888 | 6/2010 |
| CA | 2764517 | 12/2010 |
| EP | 0111144 | 10/1983 |
| EP | 0318262 | 5/1989 |
| EP | 0 640 341 | 3/1995 |
| EP | 0661045 | 5/1995 |
| EP | 698389 | 2/1996 |
| EP | 0647448 | 2/2001 |
| EP | 1293195 | 3/2003 |
| EP | 1897544 | 3/2008 |
| EP | 1897545 | 12/2008 |
| EP | 2457563 | 5/2012 |
| JP | H07-112932 | 5/1995 |
| JP | 2001-55322 | 2/2001 |
| JP | 2005-500364 | 1/2005 |
| JP | 2005-505589 | 2/2005 |
| WO | 91/07950 | 6/1991 |
| WO | 1993/10765 | 6/1993 |
| WO | 95/20947 | 8/1995 |
| WO | 97/12605 | 4/1997 |
| WO | 97/37689 | 10/1997 |
| WO | 97/48385 | 12/1997 |
| WO | 97/49384 | 12/1997 |
| WO | 99/20255 | 4/1999 |
| WO | 99/32119 | 7/1999 |
| WO | 99/32120 | 7/1999 |
| WO | 99/44591 | 9/1999 |
| WO | 2000/033835 | 6/2000 |
| WO | 2001/008661 | 2/2001 |
| WO | 2001/056544 | 8/2001 |
| WO | 2001/058447 | 8/2001 |
| WO | 2001/076576 | 10/2001 |
| WO | 2002/036099 | 5/2002 |
| WO | 2002/087558 | 11/2002 |
| WO | 2002/094254 | 11/2002 |
| WO | 03/013476 | 2/2003 |
| WO | 2003/013479 | 2/2003 |
| WO | 2003/015531 | 2/2003 |
| WO | 2003/024430 | 3/2003 |
| WO | 2003/026743 | 4/2003 |
| WO | 2003/035029 | 5/2003 |
| WO | 2003/092676 | 11/2003 |
| WO | 2004/026256 | 1/2004 |
| WO | 2004/026283 | 4/2004 |
| WO | 2004/037259 | 5/2004 |
| WO | 2005/007135 | 1/2005 |
| WO | 2005/046727 | 5/2005 |
| WO | 2005/053587 | 6/2005 |
| WO | 2006/002884 | 1/2006 |
| WO | 2007/150074 | 12/2007 |
| WO | 2007/150075 | 12/2007 |
| WO | 2008/023261 | 2/2008 |
| WO | 2009/023672 | 2/2009 |
| WO | 2009/114648 | 9/2009 |
| WO | 2010/019279 | 2/2010 |
| WO | 2010/078486 | 7/2010 |
| WO | 2010083894 | 7/2010 |
| WO | 2010/141505 | 12/2010 |
| WO | 2011154414 | 12/2011 |
| WO | 2012/076907 | 6/2012 |
| WO | 2012076907 | 6/2012 |
| WO | 2012/131463 | 10/2012 |
| WO | 2013/171146 | 11/2013 |

OTHER PUBLICATIONS

Apicella, A., "Poly(ethylene oxide)(PEO) and Different Molecular Weight PEO Blends Monolithic Devices for Drug Release," Biomaterials, vol. 14, No. 2, 1993, pp. 83-90.

Apicella, et al., "Poly(ethylene oxide)-Based Delivery Systems," Polymeric Drugs and Drug Administration, ACS Symposium Series 545, Chapter 9 (1994), pp. 111-125.

Apicella, et al. "Poly(ethylene oxide)(PEO) Constant Release Monolithic Devices," Polymers in Medicine: Biomedical and Pharmaceutical Applications, Chapter 3 (1992), pp. 23-37.

Aulton Michael E., et al., Pharmaceutics, the Science of Dosage Form Design, Reprinted 2000, pp. 1-2, 17-37, 62-80, 131-211, 304-321, 359-380, 550-677, Churchill Livingston, China.

Bettini, et al., "Translocation of drug particles in HPMC matrix gel layer: effect of drug solubility and influence on release rate," Journal of Controlled Release, vol. 70, No. 3, Feb. 2001, pp. 383-391.

Bhatia, R., "Effect of Molecular Mass, Concentration and Temperature on the Rheological Properties of Non-Newtonian Agueous Polymeric Solutions," 114, 2011, 202 pgs.

Chien, Yie W., et al., "Syringeability of Nonaqueous Parenteral Formulations—Development and Evaluation of Testing Apparatus," Journal of Parenteral Science and Technology, vol. 35, No. 6, Nov. 1981, pp. 281-284.

(56) References Cited

OTHER PUBLICATIONS

CIPO, Office Action for U.S. Pat. No. 2,900,960 dated Jun. 16, 2016.
Deighan, C.J., et al., "Rhabdomyolysis and Acute Renal Failure Resulting From Alcohol and Drug Abuse," QJ Med., vol. 93, 2000, pp. 29-33.
Dexter, M.B., et al., "The Evaluation of the Force to Expel Oily Injection Vehicles from Syringes," J. Pharm. Pharmacol., vol. 31, Aug. 1979, The Pharmaceutical Society of Great Britain, pp. 497-500.
Extended European Search Report for Application No. 14765468.5 dated Jul. 26, 2016.
Gennaro, Alfonso, Remington: The Science and Practice of Pharmacy, 20th Edition, 2000, pp. 1-3, 335-355, 654-666, 669-752, 780-820, 858-929, 995-10004, 1098-1155, 1175-1182, 13951399, 2037-2038, Lippincott Williams & Wilkins, Baltimore, MD, United States.
Handbook of Pharmaceutical Excipients, 1986, pp. 234-239, American Pharmaceutical Association, Washington D.C., United States.
Hardman, Joel G., et al., Goodman & Gilman's The Pharmacological Basis of Therapeutics, 9th Edition, 1996, pp. 3-27, 521-555, 557-577, McGraw-Hill, United States.
Hariharan, M., and Gupta, V.K., "A Novel Compression-Coated Tablet Dosage Form," Pharmaceutical Technology Yearbook, 2001, Jan. 1, 2001, pp. 14-19.
Hem, Stanley, et al., "Tissue Irritation Evaluation of Potential Parenteral Vehicles," Drug Development Communications, 1:5, 1974, pp. 471-477, Marcel Dekker, Inc.
Heng, Paul, et al., "Role of Surfactant on Drug Release from Tablets", Drug Development and Industrial Pharmacy, Oct. 20, 2008, pp. 951-962, Taylor & Francis, London, United Kingdom.
Huang, H., et al., "Preparation of Controlled Release Oral Dosage Forms by Low Temperature Melt Extrusion," The AAPS Journal, AAPS PharmaSci, 2000, 2(S1), 3 pgs.
Industrial and Engineering Chemistry I/EC, Golden Anniversary Year 50, Pattern for Progress, vol. 50, No. 1, Jan. 10, 1958, pp. 8-11, American Chemical Society, Easton, PA, United States.
International Search Report for Application No. PCT/US2014/028260 dated Jul. 25, 2014, 4 pages.
Iponz, First Examination Report for Application No. 710782 dated Apr. 28, 2016.
Kalant, H., et al., "Death in Amphetamine Users: Causes and Rates," CMA Journal, vol. 112, Feb. 8, 1975, pp. 299-304.
Kibbe, Arthur, H., "Polyethylene Oxide," Handbook of Pharmaceutical Excipients, Third Edition, 2000, pp. 399-400, PhP Pharmaceutical Press, London, United Kingdom.
Kim, C., "Drug Release from Compressed Hydrophilic POLYOX-WSR Tablets," Journal of Pharmaceutical Sciences, vol. 84, No. 3, Mar. 1995, pp 303-306.
Maggi, L., et al, "Dissolution Behaviour of Hydrophilic Matrix Tablets Containing Two Different Polyethylene Oxides (PEOs) for the Controlled Release of a Water-Soluble Drug," Biomaterials, vol. 23, pp. 1113-1119 (2002).
Medical Economics Company, Inc., The 1997 Physician's Desk Reference ("PDR") entry for Oxycontin®, 51$^{st}$ edition, Nov. 1996, Montvale, NJ pp. 2163-2164.
Meier, Barry, "U.S. Asks Painkiller Maker to Help Curb Wide Abuse," The New York Times, May 1, 2001, 3 pgs.
Modern Pharmaceutics, 3rd Edition, Drugs and The Pharmaceutical Sciences, vol. 72, 1996, pp. 21-73, 75-119, 121-153, 155-178, 333-394, 441-487, 575-609, 727-772, Marcel Dekker, Inc., United States.
Moroni, et al., "Application of Poly(oxyethylene) Homopolymers in Sustained Release Solid Formulation," Drug Dev. and Indus. Pharmacy, 21(12), pp. 1411-1428 (1995).

Philip, George, et al., "The Human Nasal Response to Capsaicin," J. Allergy Clin. Immonul., vol. 94, No. 6, Part 1, Dec. 1994, pp. 1035-1045, Mosy-Year Book, Inc., Baltimore, MD, United States.
Poynton, Charles, Digital Video and HDTV Algorithms and Interfaces, The CIE System of Colorimetry, 2003, pp. 228-229, Morgan Kaufmann Publishers, San Francisco, United States.
Prescribing Information for Concerta Extended-Release Tablets, Nov. 2010, pp. 1-9 , Ortho-McNeil-Janssen Pharmaceuticals, Inc., Titusville, United States.
Product webpage for EUDRAGIT RS 30 D [online] (Apr. 30, 2010), retrieved from the internet on (Dec. 10, 2014) from URL, http://web.archive.org/web/20100430062425/http://eudragit.evonik.com/prouct/eudragit/en/products-services/eudragit-products/sustained-release-formulations/rs-30-d/pages/default.aspx>.
Sarkar, N., "Kinetics of thermal gelation of methylcellulose and hydroxypropylmethylcellulose in aqueous solutions," Carbohydrate Polymers, vol. 26, No. 3, Jan. 1995, pp. 195-203.
Sarkar, N., "Thermal Gelation Properties of Methyl and Hydroxypropyl Methylcellulose," Journal of Polymer Science, vol. 24, No. 4, Aug. 1979, pp. 1073-1087.
Search Report for Taiwan Patent Application No. 103109308, English translation, dated May 21, 2015.
Stafford, J.W., et al., "Temperature dependence of the disintegration times of compressed tablets containing hydroxypropylcellulose as binder," Journal of Pharmacy and Pharmacology, vol. 30, No. 1, Sep. 1978, pp. 1-5, John Wiley & Sons, New York, United States.
The 1997 Physician's Desk Reference ("PDR"), 51$^{st}$ edition, Nov. 1996, pp. 955-957, 988-989, 2163-2167, 2366-2367, Medical Economics Company, Inc., Montvale, NJ, United States.
The Merck Index, 14$^{th}$ Edition, Entry Nos. 4785, 4803, 6276 and 9566, Whitehouse Station, New Jersey, USA, 2006.
Tough, Paul, "The Alchemy of Oxycontin: From Pain Relief to Drug Addiction," The New York Times, Jul. 29, 2001, 14 pgs.
U.S. Pharmacopeia & National Formulary 24/19, The Standard of Quality, United States Pharmacopeial Convention, Inc., 1999, pp. 1233-1238, 1372-1375, 1941-1951, 2002-2003, 2442-2443, 2493-2498, National Publishing, Philadelphia, PA, United States.
U.S. Pharmacopeia, p. 2206, 1995.
Vicodin®, Physcan Desk Reference, 1997, pp. 1404-1405, 51$^{st}$ Edition, Medical Economics Company, Inc., Montvale, United States.
Wilkins, Jeffrey, N., "Pharmacotherapy of Schizophrenia Patients with Comorbid Substance Abuse," Schizophrenia Bulletin, vol. 23, No. 2, 1997, pp. 215-228.
Woodburn, K.R., et al., "Vascular Complications of Injecting Drug Misuse," British Journal of Surgery, 1996, Vo. 83, p. 1329-1334.
Written Opinion of the International Searching Authority for International Application No. PCT/US2014/028260 filed on Mar. 15, 2014, dated Jul. 25, 2014, 15 pages.
Yang, et al., "Characterization of Compressibility and Compactibility of Poly(ethylene oxide) Polymers for Modified Release Application by Compaction Simulator," Journal of Pharmaceutical Sciences, vol. 85, No. 10, Oct. 1996, pp. 1085-1090.
Zhang, Feng, Dissertation: "Hot-Melt Extrusion as a Novel Technology to Prepare Sustained-Release Dosage Forms," The University of Texas at Austin, pp. v-xxv, 1-260, Dec. 1999, UMI Microform 9959618, Bell & Howell Information and Learning Company, Ann Arbor, MI, United States.
Zhang, F., et al., "Properties of Sustained-Release Tablets Prepared by Hot-Melt Extrusion," Pharmaceutical Development and Technology, vol. 4, No. 2, pp. 241-250 (1999).
Eager Polymers (Material Safety Data Sheet for CAB-O-SIL, M-5 Grade, [Retrieved from Internet <URL: http://www.eagerplastics.com/msdscabosil.htm>], (revised May 6, 2015, 5 pages).

* cited by examiner

Tamper Resistance-resistance to crushing- release from crushed granules in comparison to intact granules Alcohol Resistance

TAMPER RESISTANT PHARMACEUTICAL FORMULATIONS

FIELD OF THE INVENTION

The present invention relates to the field of pharmaceutical dosage forms that are resistant to tampering, abuse and/or alcohol dose dumping.

BACKGROUND

Pharmaceutical products are sometimes the subject of abuse. For example, a particular dose of opioid agonist may be more potent when administered parenterally as compared to the same dose administered orally. Some formulations can be tampered with to provide the opioid agonist contained therein for illicit use. Opioid agonist formulations intended for oral use are sometimes crushed or subject to extraction with solvents (e.g., ethanol) by drug abusers to provide the opioid contained therein for non-prescribed illicit use (e.g., nasal or parenteral administration).

Controlled release oral dosage forms are sought out by abusers as the crushing of the dosage form may liberate an amount of active agent otherwise intended for prolonged release (e.g., 12 to 24 hours), making it immediately available. The immediate availability upon crushing may also make controlled release dosage forms more dangerous due to the possibility of accidental overdose.

There have previously been attempts in the art to control the abuse potential associated with opioid analgesics. For example, the combination of pentazocine and naloxone has been utilized in tablets available in the United States, commercially available as Talwin® Nx from Sanofi-Winthrop. Talwin® Nx contains pentazocine hydrochloride equivalent to 50 mg base and naloxone hydrochloride equivalent to 0.5 mg base. Talwin® Nx is indicated for the relief of moderate to severe pain. The amount of naloxone present in this combination has low activity when taken orally, and minimally interferes with the pharmacologic action of pentazocine. However, this amount of naloxone given parenterally has profound antagonistic action to narcotic analgesics. Thus, the inclusion of naloxone is intended to curb a form of misuse of oral pentazocine which occurs when the dosage form is solubilized and injected. Therefore, this dosage has lower potential for parenteral misuse than previous oral pentazocine formulations. A fixed combination therapy comprising tilidine (50 mg) and naloxone (4 mg) has been available in Germany for the management of severe pain since 1978 (Valoron® N, Goedecke). The rationale for the combination of these drugs is effective pain relief and the prevention of tilidine addiction through naloxone-induced antagonisms at the morphine receptor. A fixed combination of buprenorphine and naloxone was introduced in 1991 in New Zealand (Temgesic® Nx, Reckitt & Colman) for the treatment of pain.

Commonly owned U.S. Patent Application Publication No. 20090081290 is directed to opioid formulations that are resistant to crushing in attempts to liberate the drug contained therein for illicit use.

Commonly owned U.S. Patent Application Publication No. 20030068375 is directed to opioid formulations that in certain embodiments include a gelling agent in an effective amount to impart a viscosity unsuitable for administration selected from the group consisting of parenteral and nasal administration to a solubilized mixture formed when the dosage form is crushed and mixed with from about 0.5 to about 10 ml of an aqueous liquid.

There exists a need in the art for a controlled release dosage form containing a drug susceptible to abuse that is resistant to providing an immediate release of the drug upon tampering. In the case of opioid analgesics, there exists a need for a tamper resistant formulation that does not solely rely upon the inclusion of an antagonist in the formulation to deter abuse.

All references described herein are hereby incorporated by reference in their entireties for all purposes.

OBJECTS AND SUMMARY OF THE INVENTION

It is an object of certain embodiments of the present invention to provide a solid oral dosage form comprising a drug susceptible to abuse (e.g., an opioid analgesic), which is tamper-resistant.

It is an object of certain embodiments of the present invention to provide a solid oral dosage form comprising a drug susceptible to abuse (e.g., an opioid analgesic), which is subject to less oral abuse than other dosage forms.

It is an object of certain embodiments of the present invention to provide a solid oral dosage form comprising a drug susceptible to abuse (e.g., an opioid analgesic), which is subject to less parenteral abuse than other dosage forms.

It is an object of certain embodiments of the present invention to provide a solid oral dosage form comprising a drug susceptible to abuse (e.g., an opioid analgesic), which is subject to less intranasal abuse than other dosage forms.

It is a further object of certain embodiments of the present invention to provide a solid oral dosage form comprising a drug susceptible to abuse (e.g., an opioid analgesic), which is subject to less diversion than other dosage forms.

It is a further object of certain embodiments of the present invention to provide a method of treating pain in human patients with a solid oral dosage form comprising an opioid analgesic while reducing the abuse potential of the dosage form.

It is a further object of certain embodiments of the present invention to provide a solid oral dosage form comprising a drug susceptible to abuse (e.g., an opioid analgesic), which is resistant to dose dumping in the presence of alcohol.

It is another object of certain embodiments of the present invention to provide a method of manufacturing an oral dosage form of a drug susceptible to abuse (e.g., an opioid analgesic) as disclosed herein.

It is another object of certain embodiments of the present invention to provide a use of a medicament (e.g., an opioid analgesic) in the manufacture of a tamper-resistant dosage form as disclosed herein for the treatment of a disease state (e.g., pain, diarrhea or constipation).

In other embodiments, the invention is directed to a method of preparing the solid oral dosage forms disclosed herein, e.g., in tablet or capsule form.

In further embodiments, the present invention is directed to a method of treating a disease or condition (e.g., pain, diarrhea or constipation) comprising administering to a patient in need thereof an oral dosage form as disclosed herein.

One or more of the above objects, and others can be achieved by the present invention which in certain embodiments is directed to a solid oral dosage form comprising a plurality of particles, each particle comprising a core comprising an active agent susceptible to abuse and an internal adhesion promoter, wherein the cores are dispersed in a matrix comprising a controlled release material. In other embodiments, the solid oral dosage form comprises a plurality of particles, each particle comprising (i) a core comprising an active agent susceptible to abuse and an internal adhesion promoter and (ii) a controlled release coating comprising a controlled release material layered on the core. In each embodiment, the internal adhesion promoter promotes the adhesion of the active agent and the controlled release material.

In certain embodiments, the present invention is directed to a solid oral dosage form comprising a plurality of particles, each particle comprising a core comprising an active agent susceptible to abuse, a dissolution enhancer and an internal adhesion promoter, wherein the cores are dispersed in a matrix comprising a controlled release material. In other embodiments, the solid oral dosage form comprises a plurality of particles, each particle comprising (i) a core comprising an active agent susceptible to abuse, a dissolution enhancer and an internal adhesion promoter and (ii) a controlled release coating comprising a controlled release material layered on the core.

In certain embodiments, the present invention is directed to a solid oral dosage form comprising a plurality of particles, each particle comprising a core comprising an active agent susceptible to abuse and an internal adhesion promoter, wherein the cores are dispersed in a matrix comprising a controlled release material and a pore former. In other embodiments, the solid oral dosage form comprises a plurality of particles, each particle comprising (i) a core comprising an active agent susceptible to abuse, an internal adhesion promoter and a dissolution enhancer and (ii) a controlled release coating comprising a controlled release material and a pore former, layered on the core.

In certain embodiments, the present invention is directed to a solid oral dosage form comprising a plurality of particles, each particle comprising a core comprising an active agent susceptible to abuse, a dissolution enhancer and an internal adhesion promoter, wherein the cores are dispersed in a matrix comprising a controlled release material and an alcohol resistant material. In one embodiment, the cores can first be dispersed in the controlled release material (and optional pore former) with the resultant dispersion further dispersed in the alcohol resistant material or vice versa. In another embodiment, the cores can be dispersed simultaneously with both the controlled release material and the alcohol resistant material. In other embodiments, the solid oral dosage form comprises a plurality of particles, each particle comprising (i) a core comprising an active agent susceptible to abuse, an internal adhesion promoter and a dissolution enhancer, (ii) a controlled release coating comprising a controlled release material and a pore former, layered on the core and (iii) an alcohol resistant coating comprising an alcohol resistant material layered over the controlled release coating.

In certain embodiments, the present invention is directed to a solid oral dosage form comprising a plurality of particles, each particle comprising a core comprising an active agent susceptible to abuse, a dissolution enhancer and an internal adhesion promoter, wherein the core is dispersed in a matrix comprising a controlled release material, an alcohol resistant material and an external adhesion promoter. In one embodiment, the cores can first be dispersed in the controlled release material (and optional pore former) with the resultant dispersion further dispersed in the alcohol resistant material and external adhesion promoter (or vice versa). In another embodiment, the cores can be dispersed simultaneously with the controlled release material and the alcohol resistant material (and the optional external adhesion promoter). In other embodiments, the solid oral dosage form comprises a plurality of particles, each particle comprising (i) a core comprising an active agent susceptible to abuse, an internal adhesion promoter and a dissolution enhancer, (ii) a controlled release coating comprising a controlled release material and a pore former, layered on the core and (iii) an alcohol resistant coating comprising an alcohol resistant material and an external adhesion promoter layered over the controlled release coating.

In certain embodiments, the present invention is directed to a solid oral dosage form comprising a plurality of particles, each particle comprising a core comprising an opioid agonist and a carbomer, wherein the core is dispersed in a matrix comprising a neutral acrylic polymer, a pore former, an alkylcellulose and a carbomer. In one embodiment, the cores can first be dispersed in the neutral acrylic polymer (and optional pore former) with the resultant dispersion further dispersed in the alkylcellulose (and optional carbomer) (or vice versa). In another embodiment, the cores can be dispersed simultaneously with the neutral acrylic polymer and the alkylcellulose. In other embodiments, the solid oral dosage form comprises a plurality of particles, each particle comprising (i) a core comprising an opioid agonist and a carbomer; (ii) a controlled release coating comprising a neutral acrylic polymer and a pore former; and (iii) an alcohol resistant coating comprising an alkylcellulose and a carbomer.

In certain embodiments, the present invention is directed to a process for preparing a solid oral dosage form comprising preparing a plurality of particles by (i) granulating an opioid agonist and a carbomer to form core granules; (ii) mixing, granulating or coating the core granules with a neutral acrylic polymer and a pore former (e.g., lactose) to obtain controlled release particles (e.g., granules); (iii) mixing, granulating or coating the controlled release particles with methylcellulose and a carbomer to obtain alcohol resistant controlled release particles (e.g., granules); and (iv) compressing the alcohol resistant controlled release particles into a tablet or filling the particles in a capsule.

In certain embodiments, the solid oral dosage forms disclosed herein provide a controlled release of the active agent contained therein such that the dosage form is suitable for administration on a once daily (Q.D.) or twice daily (B.I.D.) basis.

In describing the present invention, the following terms are to be used as indicated below. As used herein, the singular forms "a," "an," and "the" include plural references unless the context clearly indicates otherwise. Thus, for example, reference to "a drug susceptible to abuse" includes a single active agent as well as a mixture of two or more different active agents, and reference to a "gelling agent" includes a single gelling agent as well as a mixture of two or more different gelling agents, and the like.

As used herein, the terms "active agent," "active ingredient," "pharmaceutical agent," and "drug" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, and all complexes, stereoisomers, crystalline forms, amorphous form, co-crystals, ether, esters, hydrates and solvates thereof, and mixtures thereof, which produce the intended effect.

As used herein, the terms "therapeutically effective" refers to the amount of drug or the rate of drug administration needed to produce a desired therapeutic result.

As used herein, the terms "prophylactically effective" refers to the amount of drug or the rate of drug administration needed to produce a desired prophylactic result.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is non-superimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "patient" means a subject who has presented a clinical manifestation of a particular symptom or symptoms suggesting the need for treatment, who is treated preventatively or prophylactically for a condition, or who has been diagnosed with a condition to be treated.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, dicyclohexylamine salt, N,N'-dibenzylethylenediamine salt and the like.

The term "subject" is inclusive of the definition of the term "patient" and does not exclude individuals who are entirely normal in all respects or with respect to a particular condition.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

The term "recovery" means the amount of drug obtained from the resultant solution of a tampered dosage form (e.g., crushing and mixing in 5 or 10 mL solvent) upon aspiration with a 27 gauge needle. In other embodiments the needle can be a different gauge, e.g., 18 gauge, 22 gauge or 25 gauge.

The term "tampering" means a manipulation by mechanical, thermal, and/or chemical means to obtain a solution of drug available for illicit use. The tampering can be, e.g., by means of crushing and mixing then dosage form with a solvent (with or without heat), or by dissolution of an intact dosage form in a solvent (with or without heat).

The term "adhesion promoter" means a compound that maintains an interaction (e.g., chemical or physical) between two other compounds to maintain a desired characteristic of the interacted compounds. For example, an adhesion promoter of the present invention (e.g., carbomer, either internally or externally) maintains the interaction between the active agent and the controlled release material such that a controlled release of the active agent is maintained, even when the dosage form is crushed in an attempt to liberate the active agent for an immediate release. In another example, an adhesion promoter of the present invention (e.g., carbomer either internally or externally) maintains the interaction between the controlled release material and the alcohol resistant material such that the dosage form does not dose dump in the presence of alcohol.

The term "internal adhesion promoter" means a compound that is an adhesion promoter and is contained in the core of the dosage forms disclosed herein.

The term "external adhesion promoter" means a compound that is an adhesion promoter and is contained outside the core of the dosage forms disclosed herein

DETAILED DESCRIPTION

Figure 1A:
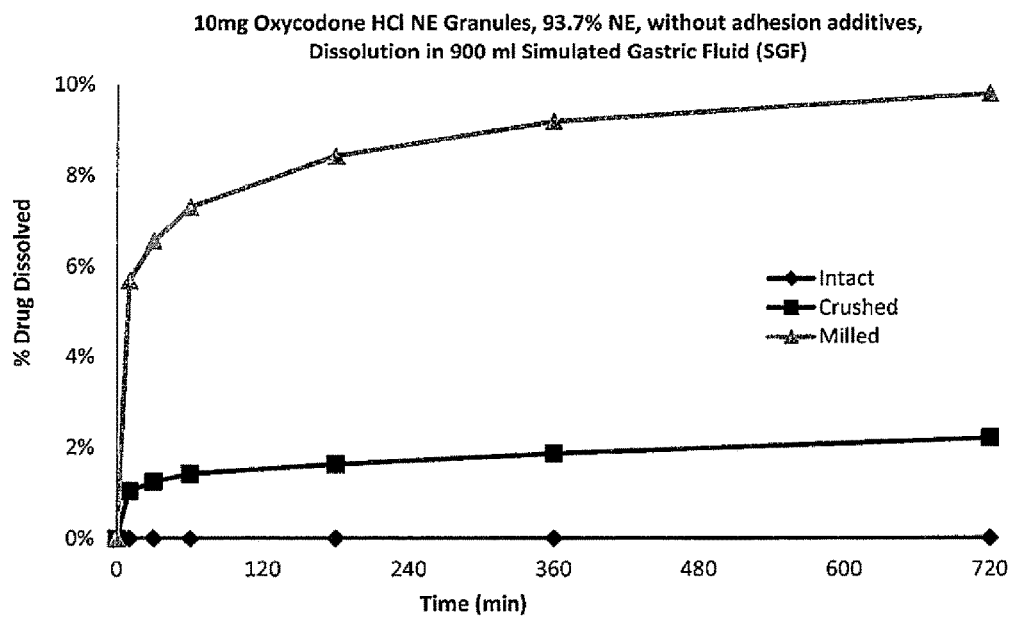
FIG. 1A depicts a graphical representation of crush resistance of a formulation without an adhesion promoter.
Figure 1B:
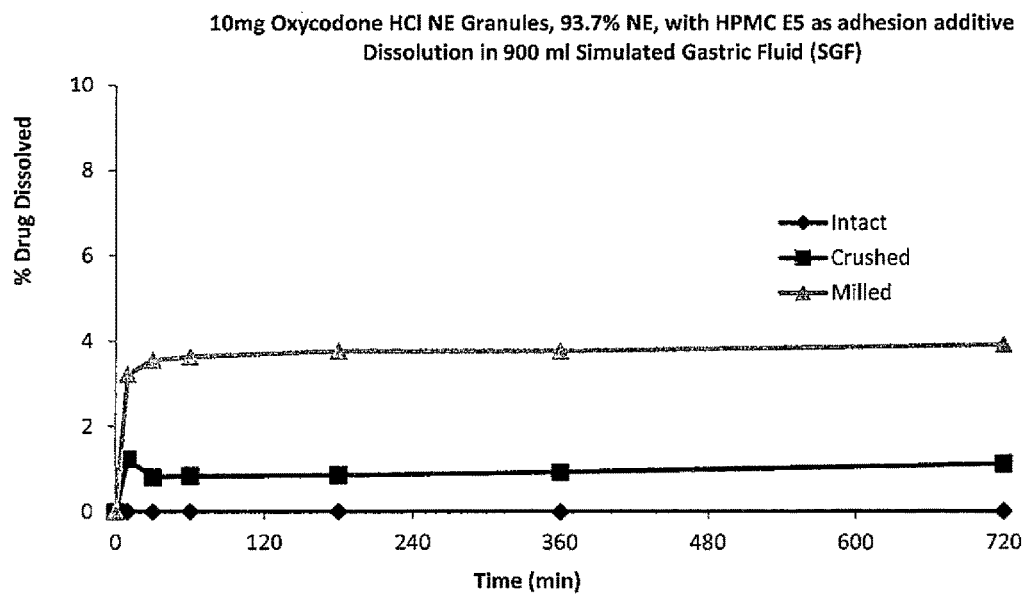
FIG. 1B depicts a graphical representation of crush resistance of a formulation with HPMC as the adhesion promoter.
Figure 1C:
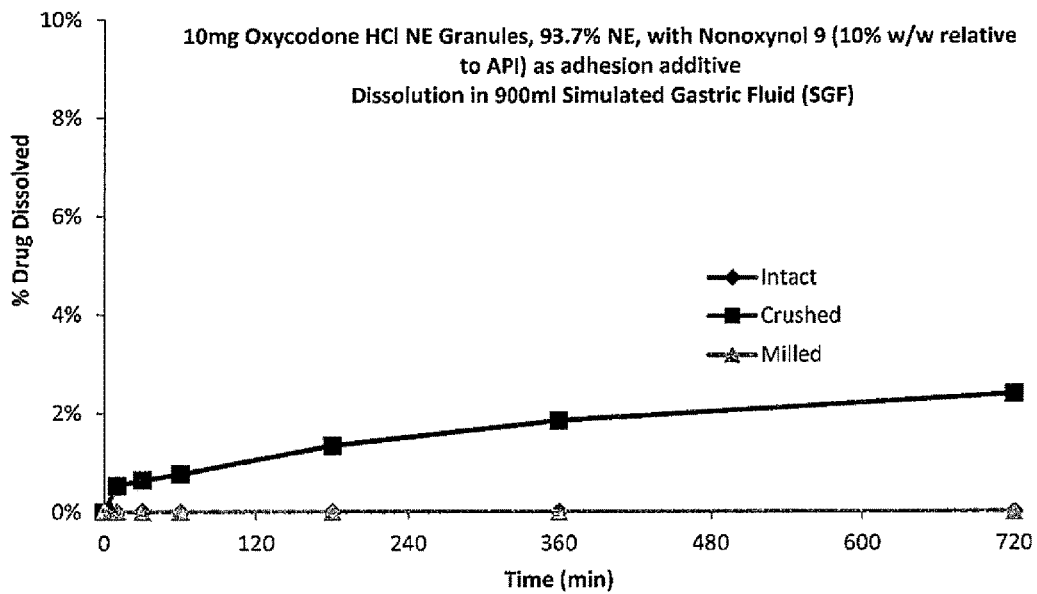
FIG. 1C depicts a graphical representation of crush resistance of a formulation with Nonoxynol 9 as the adhesion promoter.
Figure 1D:
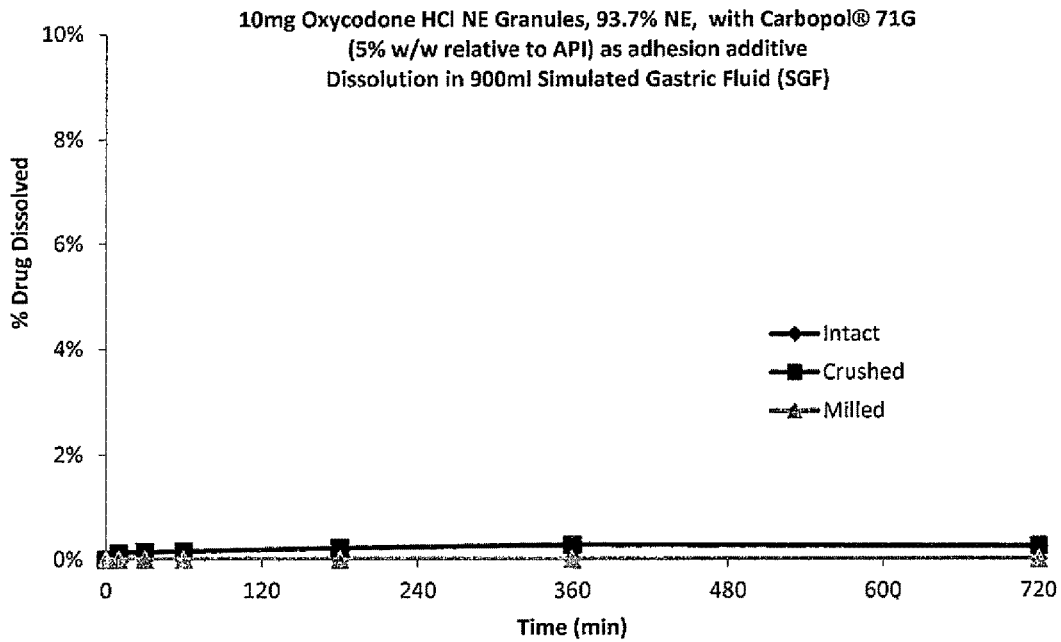
FIG. 1D depicts a graphical representation of crush resistance of a formulation with Carbopol® 71G as the adhesion promoter.

Controlled release dosage forms play a vital part in the management of both acute and chronic conditions (e.g., pain management with opioid analgesics). Therefore, it is important to provide a tamper-resistant controlled release dosage form of a drug susceptible to abuse that may be utilized to provide effective plasma levels to a patient according to an intended release profile, while not being susceptible to significant dose dumping when the dosage form is crushed, milled or tampered with by other means in an attempt to liberate the active agent contained therein for illicit use.

In certain embodiments, the dosage forms contained herein provide an in-vitro dissolution of the active agent contained therein indicative of a controlled release profile such that it can be administered on a once daily or twice daily basis. By virtue of the present invention, when the dosage form is crushed according to the methods disclosed herein, the in-vitro dissolution profile is maintained, decreased or not significantly increased (e.g., by no more than a 30% increase at 1 hour), such that the administration of a crushed dosage form would not likely provide any more of a euphoric effect than the administration of an intact dosage form.

In certain embodiments, the dosage forms contained herein provide an in-vitro dissolution of the active agent contained therein indicative of a controlled release profile and when the dosage form is subject to dissolution in an alcohol containing solvent (e.g., SGF with 40% EtOH) according to the methods disclosed herein, the in-vitro dissolution profile is maintained, decreased or not significantly increased (e.g., by no more than a 20% increase at 1 hour), such that the administration of dosage form with alcohol would not dose dump and would not likely provide any more of a euphoric effect than the administration of an intact dosage form. This attribute would also deter the tampering of the dosage form by dissolution in an alcohol containing solvent in an attempt to liberate the active agent contained therein for illicit use.

In certain embodiment, the present invention is directed to a solid oral dosage form comprising a plurality of particles, each particle comprising a core comprising an active agent susceptible to abuse and an internal adhesion promoter, wherein the cores are dispersed in a matrix comprising a controlled release material. In other embodiments, the solid oral dosage form comprises a plurality of particles, each particle comprising (i) a core comprising an active agent susceptible to abuse (e.g., an opioid agonist) and (ii) a controlled release coating comprising a controlled release material layered on the core. The core may further comprise an internal or external adhesion promoter to promote the adhesion of the active agent and the controlled release material such that a controlled release profile is provided or maintained when the dosage form is administered intact and/or the dissolution profile is maintained or not significantly changed when the dosage form is tampered with in an attempt to liberate the active agent contained thereof or illicit use.

The core of the particles can also contain a dissolution enhancer to balance the controlled release provided by the controlled release material, such that enough active agent is released from the dosage form to provide a desired release profile and pharmacodynamic response.

In addition to, or in place of the dissolution enhancer in the dosage form, the controlled release coating of the particles may include a pore former, that also may act to enhance the release of the active agent contained therein such that enough active agent is released from the dosage form to provide a desired release profile and pharmacodynamic response.

In embodiments that are resistant to dissolution in alcohol containing solvents, such resistance can be provided by an alcohol resistant material mixed or granulated with, or coated over the controlled release material. The alcohol resistant material may further comprise an external adhesion promoter to provide or enhance adhesion of the alcohol resistant material and the controlled release material in order to obtain, enhance or maintain the alcohol resistance characteristics of the dosage form.

In certain embodiments, the controlled release material is a polymer that can modify the release rate of the active agent contained therein. Examples of polymers that can be utilized to modify the release of the active agent include pharmaceutically acceptable cellulosic polymers, including but not limited to alkyl celluloses, cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates and mixtures thereof.

In other embodiments of the present invention, the controlled release polymer is a pharmaceutically acceptable acrylic polymer selected without limitation from acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), glycidyl methacrylate copolymers, and mixtures of any of the foregoing. Preferably, the acrylic polymer is a neutral acrylic polymer (e.g., Eudragit® NE 30 D, Eudragit® NE 40 D or Eudragit® NM 30 D), which can also provide crush-resistant characteristics to the individual particles. However, when the particles are crush resistant and compressed into a tablet, the tablet breaks apart wherein the tablet is subject to a typical force used in tampering. In certain embodiments, the tablet has a breaking strength of less than about 400N, less than about 350N, less than about 300N or less than about 250N.

The internal adhesion promoter may be selected from the group consisting of a cellulosic material, a surfactant, a carbomer and a mixture thereof. In certain embodiments, the cellulosic material used as an internal adhesion promoter is hydroxypropylmethylcellulose. In certain embodiments, the surfactant used as an internal adhesion promoter is a nonionic surfactant such as a nonoxynol (e.g., nonoxynol-9) or a sorbitan ester (e.g., Span® 20) and a mixture thereof.

In a particular embodiment, the internal adhesion promoter is an anionic polymer such as a polyacrylic acid. The polyacrylic acid can be a homopolymer and can be optionally crosslinked with a crosslinking agent (referred to as a carbomer). The cross-linking agent can be a polyalcohol allyl ether such as an allyl ether pentaerythritol, an allyl ether of sucrose, an allyl ether of propylene or a mixture thereof.

The dissolution enhancer, when utilized in the present invention, can be a pharmaceutically acceptable cellulosic polymer, including but not limited to alkyl celluloses, cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates and mixtures thereof. In a particular embodiment, the dissolution enhancer is methylcellulose. The dissolution enhancer can also be a sugar (e.g., lactose or mannitol), a starch (e.g., sodium starch glycolate) or a polymer (e.g., crospovidone).

The pore former, when utilized in the present invention, can be a water soluble material that enhances release by creating channels or passageways in the controlled release coating, or by otherwise weakening the integrity of the coating upon exposure to an environmental fluid. The pore former can be a polysaccharide such as lactose, sucrose, dextrose, mannitol, d-mannitol, alpha-d-lactose monohydrate, glucose or mixture thereof, a cellulosic material such as microcrystalline cellulose, hydroxypropylmethylcellulose or a mixture thereof, or a material such as polyvinyl alcohol. The pore former can also be a water soluble polymer such as polyethylene glycol, povidone, poloxamer and combinations thereof. The pore former can also be an organic solvent such as propylene glycol. Other materials that can be pore formers include osmagents or osmotic agents such as organic and inorganic compounds. Such agents can include salts, acids, bases, chelating agents, sodium chloride, calcium sulfate, calcium phosphate, lithium chloride, magnesium chloride, magnesium sulfate, lithium sulfate, potassium chloride, sodium sulfite, calcium bicarbonate, sodium sulfate, calcium lactate, urea, tartaric acid, raffinose, and combinations thereof.

More specifically, the pore former can be a salt which is water-soluble and pharmaceutically acceptable. The cations of these salts can be alkali metals such as sodium and potassium, alkaline earth metals such as magnesium, calcium and barium, or other cations such as ammonium, ferric, etc. The anions may include 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, ascorbic acid (L), aspartic acid (L), benzenesulfonic acid, benzoic acid, camphoric acid (+), camphor-10-sulfonic acid (+), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, glucoheptonic acid (D), gluconic acid (D), glucuronic acid (D), glutamic acid, glutaric acid, glycerophosphoric acid, glycolic acid, hippuric acid, hydrobromic acid, hydrochloric acid, isobutyric acid, lactic acid (DL), lactobionic acid, lauric acid, maleic acid, malic acid (−L), malonic acid, mandelic acid (DL), methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, pyroglutamic acid (−L), salicylic acid, sebacic acid, stearic acid, succinic acid, sulfuric acid, tartaric acid (+L), thiocyanic acid, toluenesulfonic acid (p) and undecylenic acid.

The alcohol resistant material utilized in the present invention can be any pharmaceutically acceptable material that is capable of providing resistance to dissolution in an alcohol containing solvent. The alcohol resistant material may be an alkylcellulose such as methylcellulose.

The external adhesion promoter may be selected from the group consisting of a cellulosic material, a surfactant, a carbomer and a mixture thereof. The external adhesion promoter can be the same or different than the internal adhesion promoter. In certain embodiments, the cellulosic material used as an external adhesion promoter is hydroxypropylmethylcellulose. In certain embodiments, the surfactant used as an external adhesion promoter is a non-ionic surfactant such as a nonoxynol (e.g., nonoxynol-9) or a sorbitan ester (e.g., Span® 20) and a mixture thereof.

In a particular embodiment, the external adhesion promoter is an anionic polymer such as a polyacrylic acid. The polyacrylic acid can be a homopolymer and can be optionally crosslinked with a crosslinking agent (a carbomer). The cross-linking agent can be a polyalcohol allyl ether such as an allyl ether pentaerythritol, an allyl ether of sucrose, an allyl ether of propylene or a mixture thereof.

A unit dose of a plurality of particles of the present invention can be administered in any suitable form, e.g., in a capsule (e.g., a gelatin capsule), contained in a powder paper, or compressed into a tablet.

The dosage forms of the present invention can be prepared by mixing the active agent and the adhesion promoter together to form a plurality of cores. The cores can be prepared by granulating the materials to form core granules, by compression of a mixture of the components, or by layering the components over an inert substance such as non-pareil beads.

The core granules can then be mixed, granulated or coated with the controlled release material and the optional pore former to obtain controlled release particles. This process may include spray coating the core particles (e.g., core granules) with the controlled release material and optional pore former or by granulating the core particles with the controlled release material and optional pore former.

The controlled release particles can then be mixed, granulated or coated with alcohol resistant material to obtain alcohol resistant controlled release particles. This process may include spray coating the controlled release particles (e.g., controlled release granules) with the alcohol resistant material and optional external adhesion promoter or by granulating the controlled release particles with the alcohol resistant material and optional external adhesion promoter.

The alcohol resistant controlled release particles can then be contained within a pharmaceutically acceptable capsule or compressed into a tablet.

In certain embodiments, the weight ratio of the active agent to the controlled release material is from about 2:1 to about 1:100; from about 1:5 to about 1:50; from about 1:1 to about 1:75 or from about 1:10 to about 1:30.

In certain embodiments, the particles can have a mean diameter from about 0.1 mm to about 2 mm; from about 0.2 mm to about 1 mm; or from about 0.3 mm to about 0.8 mm.

In certain embodiments, the solid oral dosage form of the present invention comprises from about 0.1% to about 80% (w/w) active agent; from about 0.5% to about 60% (w/w) active agent; from about 1% to about 40% (w/w) active agent; from about 0.1% to about 30% (w/w) active agent; from about 0.5% to about 20% (w/w) active agent; from about 1% to about 10% (w/w) active agent or from about 1% to about 5% active agent.

In certain embodiments, the solid oral dosage form of the present invention comprises from about 10% to about 90% (w/w) controlled release material; from about 25% to about 75% (w/w) controlled release material; or from about 40% to about 60% (w/w) controlled release material.

In certain embodiments, the solid oral dosage form of the present invention comprises from about 0.05% to about 10% (w/w) internal adhesion promoter; from about 0.1% to about 5% (w/w) internal adhesion promoter; or from about 0.5% to about 3% (w/w) internal adhesion promoter.

In certain embodiments, the solid oral dosage form of the present invention comprises from about 1% to about 40% (w/w) dissolution enhancer; from about 5% to about 30% (w/w) dissolution enhancer; or from about 10% to about 20% (w/w) dissolution enhancer.

In certain embodiments, the solid oral dosage form of the present invention comprises from about 0.5% to about 25% (w/w) pore former; from about 1% to about 15% (w/w) pore former; or from about 2% to about 10% (w/w) pore former.

In certain embodiments, the solid oral dosage form of the present invention comprises from about 1% to about 50% (w/w) alcohol resistant material; from about 5% to about 40% (w/w) alcohol resistant material; or from about 10% to about 30% (w/w) alcohol resistant material.

In certain embodiments, the solid oral dosage form of the present invention comprises from about 0.5% to about 15% (w/w) external adhesion promoter; from about 1% to about 10% (w/w) external adhesion promoter; or from about 2% to about 8% (w/w) external adhesion promoter.

In certain embodiments, the solid oral dosage form of the present invention provides a dissolution release rate in-vitro of the active agent, when measured by the USP Type 2, Paddle Method at 50 rpm in 900 ml Simulated Gastric Fluid (SGF) without enzymes at 37° C. of at least about 15% by weight of the active agent released at 1 hour, from about 25% to about 65% by weight of the active agent released at 2 hours, from about 45% to about 85% by weight of the active agent released at 4 hours, and at least about 60% by weight of the active agent released at 8 hours.

In certain embodiments, the solid oral dosage form of the present invention provides a dissolution release rate in-vitro of the active agent, when measured by the USP Type 2, Paddle Method at 50 rpm in 900 ml Simulated Gastric Fluid (SGF) without enzymes at 37° C. of at least about 20% by weight of the active agent released at 4 hours, from about 20% to about 65% by weight of the active agent released at 8 hours, from about 45% to about 85% by weight of the active agent released at 12 hours, and at least about 80% by weight of the active agent released at 24 hours.

In certain embodiments, the amount of active agent released from the dosage forms of the present invention at 0.5 hour, 1 hour, 2 hours and/or 4 hours when measured in a USP Type 2, Paddle Method at 50 rpm in 900 ml simulated gastric fluid (SGF) without enzymes with 40% ethanol at 37° C., is within 30% (higher or lower) of the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released from the dosage forms of the present invention at 0.5 hour, 1 hour, 2 hours and/or 4 hours when measured in a USP Type 2, Paddle Method at 50 rpm in 900 ml simulated gastric fluid (SGF) without enzymes with 40% ethanol at 37° C., is within 25% (higher or lower) of the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released from the dosage forms of the present invention at 0.5 hour, 1 hour, 2 hours and/or 4 hours when measured in a USP Type 2, Paddle Method at 50 rpm in 900 ml simulated gastric fluid (SGF) without enzymes with 40% ethanol at 37° C., is within 20% (higher or lower) of the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released from the dosage forms of the present invention at 0.5 hour, 1 hour, 2 hours and/or 4 hours when measured in a USP Type 2, Paddle Method at 50 rpm in 900 ml simulated gastric fluid (SGF) without enzymes with 40% ethanol at 37° C., is within 10% (higher or lower) of the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released from the dosage forms of the present invention at 0.5 hour, 1 hour, 2 hours and/or 4 hours when measured in a USP Type 2, Paddle Method at 50 rpm in 900 ml simulated gastric fluid (SGF) without enzymes with 40% ethanol at 37° C., is within 5% (higher or lower) of the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released at 0.5 hour, 1 hour, 2 hours or 4 hours when measured in a USP Type 2, Paddle Method at 50 rpm in 900 ml simulated gastric fluid (SGF) without enzymes with 40% ethanol at 37° C., is less than the amount of active agent released at the same time period when measured in a USP Type 2, Paddle Method at 50 rpm in 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 30% (higher or lower) of the amount of active agent released from an intact dosage form at the same time period when measured in a USP Type 2, Paddle Method at 50 rpm in 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 25% (higher or lower) of the amount of active agent released from an intact dosage form at the same time period when measured in a USP Type 2, Paddle Method at 50 rpm at 100 rpm in 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 20% (higher or lower) of the amount of active agent released from an intact dosage form at the same time period when measured in a USP Type 2, Paddle Method at 50 rpm in 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 15% (higher or lower) of the amount of active agent released from an intact dosage form at the same time period when measured in a USP Type 2, Paddle Method at 50 rpm in 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 10% (higher or lower) of the amount of active agent released from an intact dosage form at the same time period when measured in a USP Type 2, Paddle Method at 50 rpmin 900 ml simulated gastric fluid without enzymes (SGF) with 0% ethanol at 37° C.

In certain embodiments, the amount of active agent released from a crushed dosage form at 0.5 hour, 1 hour, 2 hours or 4 hours when measured in a USP Type 2, Paddle Method at 50 rpm in 900 ml simulated gastric fluid (SGF) without enzymes at 37° C., is within 5% (higher or lower) of the amount of active agent released from an intact dosage form at the same time period when measured in a USP Type 2, Paddle Method at 50 rpm in 900 ml simulated gastric fluid without enzymes (SGF) with 0% ethanol at 37° C.

The dosage forms of the present invention can include additional excipients in order to, e.g., aid manufacturing, provide additional tamper resistance, further modify the release rate, or further modify alcohol resistance.

Additional excipients may include at least one excipient selected from the group consisting of bulking agents or fillers, plasticizers, stabilizers, diluents, lubricants, disintegrants, binders, granulating aids, colorants, flavorants, anti-oxidants, and glidants.

Suitable anti-oxidants include organic acids, carboxylic acids, acid salts of amino acids, sodium metabisulphite, ascorbic acid and its derivatives, malic acid, isoascorbic acid, citric acid, tartaric acid, sodium sulphite, sodium bisulphate, tocopherol, water- and fat-soluble derivatives of tocopherol, sulphites, bisulphites and hydrogen sulphites, butylated hydroxyanisol (BHA) or butylated hydroxytoluene (BHT), 2,6-di-t-butyl-alpha-dimethylamino-p-cresol, t-butylhydroquinone, di-t-amylhydroquinone, di-t-butylhydroquinone, butylhydroxytoluene, butylhydroxyanisole, pyrocatechol, pyrogallol, propyl gallate, and nordihydroguaiaretic acid, phosphoric acids, sorbic and benzoic acids, esters, derivatives and isomeric compounds, vitamin E, ascorbyl palmitate, ethylenediaminetetraacetic acid, cysteine, pharmaceutically acceptable salts thereof, and mixtures thereof. Specific combinations of anti-oxidants include BHT and BHA; BHA and propyl gallate; BHT, BHA and sodium metabisulphite; BHA and citric acid; vitamin E and ascorbyl palmitate; and BHA, BHT and ethylenediaminetetraacetic acid.

The drug susceptible to abuse can be dry-blended with the internal adhesion promoter and any additional excipients prior to being formed into core particles. In certain embodiments, the materials can be wet-granulated, dried, and optionally milled to prepare the core particles.

In certain embodiments, the controlled release material can be included in the core particles, alternatively, or in addition to, the controlled release matrix or coating. The controlled release matrix or coating can include one or more controlled release materials and optional pore former and be mixed with, granulated with or layered over the core particles to achieve a weight gain, e.g., of from about 1% to about 500%, from about 25% to about 400%, or from about 50% to about 300% (w/w).

The dosage forms can also include a coating to enhance cosmetic appearance and/or to reduce tackiness. Examples of materials to be utilized as a film coat include hydroxypropylmethylcellulose, polyvinyl alcohol, lactose, and mixtures thereof. The film coat can be: (i) an outer coating directly coated onto a dosage form (e.g., a compressed tablet or an individual particle), or (ii) an intermediate coating between the core and the controlled release matrix or coating and/or the controlled release matrix or coating and the alcohol resistant matrix or coating.

In certain embodiments, the plurality of particles can be combined with additional excipients prior to being compressed into a tablet. Such additional excipients can be disintegrants, fillers, flow aids, lubricants and gelling agents. The gelling agent can be in an amount to be an aversive agent by forming a viscous solution upon introduction with a small amount of a solvent. The resultant viscosity would hinder the ability to have the active agent contained therein administered by the parenteral or nasal route.

The disintegrant can be an agent such as, e.g., polyvinylpyrrolidone, sodium starch glycolate, crosscarmellose sodium, or a mixture thereof. The filler or diluent can be an agent such as, e.g., lactose, dextrose, mannitol, microcrystalline cellulose, or a mixture thereof.

The gelling agent utilized in certain embodiments of the present invention can be selected from sugars, sugar derived alcohols (e.g., mannitol, sorbitol, and the like), starch and starch derivatives, cellulose derivatives (e.g., microcrystalline cellulose, sodium carboxymethyl cellulose, methylcellulose, ethyl cellulose, hydroxyethyl cellulose, hydroxypropyl cellulose, and hydroxypropyl methylcellulose), attapulgites, bentonites, dextrins, alginates, carrageenan, gums (e.g., gum tragacanth, gum acacia, guar gum, and xanthan gum), pectin, gelatin, kaolin, lecithin, magnesium aluminum silicate, polyvinylpyrrolidone, polyethylene glycol, polyethylene oxide, polyvinyl alcohol, silicon dioxide, curdlan, furcelleran, egg white powder, lacto albumin, soy protein, chitosan, surfactants, mixed surfactant/wetting agent systems, emulsifiers, other polymeric materials, and mixtures thereof. In certain embodiments, the gelling agent is xanthan gum. In other embodiments, the gelling agent is pectin. The pectin or pectic substances include purified or isolated pectates and crude natural pectin from sources such as apple, citrus or sugar beet residues which have been subjected, when necessary, to esterification or de-esterification (e.g., by alkali or enzymes). The pectins may also be derived from citrus fruits such as lime, lemon, grapefruit, and orange. In particular embodiments, the gelling agent may be selected from the group consisting of pregelatinized starch (e.g., Swelstar® from Asahi Kasei), hydroxyethylcellulose (e.g., Natrosol® from Ashland Inc.), guar gum (e.g., Supercol® from Ashland Inc.), xanthan gum, alginate, carrageenan, polyethylene oxide and a mixture thereof.

In addition to gelling agents, the dosage forms of the present invention can include other aversive agents to further deter the illicit use of the drug contained therein. These other aversive agents can be, e.g., an emetic, an antagonist, a bittering agent, an irritant, or a mixture thereof. They can be incorporated into the particles, or added separately within a capsule or as additional tableting excipients.

The emetic may be selected from, e.g., the group consisting of methyl cephaeline, cephaeline, emetine hydrochloride, psychotrine, O-methylpsychotrine, emetamine, ipecamine, hydro-ipecamine, ipecacunhic acid and mixtures thereof. In particular embodiments, the emetic is ipecac.

The antagonist may be selected from, e.g., the group consisting of naltrexone, naloxone, nalmefene, cyclazacine, levallorphan, pharmaceutically acceptable salts thereof, and mixtures thereof.

The bittering agent may be selected from, e.g., the group consisting of flavor oils, flavoring aromatics, oleoresins, plant extracts, leaf extracts, flower extracts, fruit extracts, sucrose derivatives, chlorosucrose derivatives, quinine sulphate, denatonium benzoate and mixtures thereof. In certain embodiments, the bittering agent is spearmint oil, peppermint oil, eucalyptus oil, oil of nutmeg, allspice, mace, oil of bitter almonds, menthol or a mixture thereof. In other embodiments, the bittering agent extracted from a fruit is selected from the group consisting of lemon, orange, lime, grapefruit, and mixtures thereof. In a particular embodiment, the bittering agent is denatonium benzoate.

The irritant may be selected from, e.g., a surfactant, capsaicin or a capsaicin analog. The capsaicin analog can be selected from the group consisting of resiniferatoxin, tinyatoxin, heptanoylisobutylamide, heptanoyl guaiacylamide, an isobutylamide, a guaiacylamide, dihydrocapsaicin, homovanillyl octylester, nonanoyl vanillylamide, and mixtures thereof.

The surfactant can be selected from the group consisting of poloxamer, a sorbitan monoester, a glyceryl monooleate, sodium lauryl sulfate and mixtures thereof.

The surfactant can be included in the dosage form in an amount, e.g., from about 1% to about 25% (w/w) of the dosage form; from about 4% to about 15% (w/w) of the dosage form; from about 2.5% to about 10% (w/w) of the dosage form or from about 8% to about 12% (w/w) of the dosage form.

In embodiments using gelling agents, the solid oral dosage forms of the present invention when mixed or crushed and mixed (with or without heat) with from about 0.5 to about 10 ml of distilled water, provides a viscosity that prevents or reduces the ability of the drug from being drawn up into a syringe, or systemically absorbed when parenteral or nasal administration is attempted.

In certain embodiments, the viscosity after tampering with from about 0.5 to about 10 ml of distilled water is at least about 10 cP, at least about 50 cP, at least about 100 cP, at least about 500 cP or at least about 1,000 cP.

In certain embodiments, the viscosity after tampering with from about 0.5 to about 10 ml of distilled water is from about 50 cP to about 100,000 cP; from about 75 cP to about 50,000 cP; from about 100 cP to about 25,000 cP; from about 150 cP to about 10,000 cP; from about 200 cP to about 5,000 cP; or from about 250 cP to about 1,000 cP.

In certain embodiments, the recovery of the drug is, e.g., less than about 50%, less than about 40%, less than about 30%, less than about 20%, less than about 10%, less than about 8%, less than about 6%, less than about 4%, less than about 2%, less than about 1%, less than about 0.8%, less than about 0.6%, less than about 0.4%, or less than less than about 0.2%, based on a syringability test whereby the dosage form is mixed or crushed and mixed with 5 or 10 mL solvent and the resultant solution is aspirated with a 18, 22, 25 or 27 gauge needle.

The solvent utilized in the syringability test can be, e.g., tap water, distilled water, sterile saline, vinegar or 40% ethanol. Also, during the syringability test, the solvent (before or after mixing with the dosage form) can be subject to heat from any source such as, e.g., by the use of a butane lighter.

In certain embodiments of the present invention, the recovery of the drug is, e.g., less than about 10%, less than about 8%, less than about 6%, less than about 4%, less than about 2%, less than about 1%, less than about 0.8%, less than about 0.6%, less than about 0.4%, or less than less than about 0.2%, based on both heated and unheated syringability tests, whereby the dosage form is mixed or crushed and mixed with 5 or 10 mL solvent and the resultant solution is aspirated with a 18, 22, 25 or 27 gauge needle.

In certain embodiments, the ratio of extraction from an unheated syringability test to a heated syringability test is from about 1:5 to about 5:1; from about 1:4 to about 4:1; from about 1:3 to about 3:1; from about 1:2 to about 2:1; from about 1:1.5 to about 1.5:1; from about 1:1.3 to about 1.3:1 or from about 1:1.1 to about 1.1:1.

In certain embodiments of the present invention, the recovery of the drug from small volume extraction at 10 minutes and/or 60 minutes is, e.g., less than about 90%, less than about 80%, less than about 70%, less than about 60%, less than about 50%, less than about 40%, less than about 30%, less than about 20%, less than about 10%, less than about 8%, less than about 6%, less than about 4%, less than about 2%, less than about 1%, less than about 0.8%, less than about 0.6%, less than about 0.4%, or less than less than about 0.2%, based on both heated and unheated extraction tests, whereby the dosage form is mixed or crushed and mixed with 30 mL of a solvent. The small volume extraction can be measured, e.g., by the procedures of Example 3.

In certain embodiments, the ratio of extraction from an unheated small volume extraction test at 10 minutes and/or 60 minutes to a corresponding heated extraction test is from about 1:50 to about 50:1; from about 1:40 to about 40:1; from about 1:30 to about 30:1; from about 1:20 to about 20:1; from about 1:10 to about 10:1; from about 1:5 to about 5:1; from about 1:4 to about 4:1; from about 1:3 to about 3:1; from about 1:2 to about 2:1; from about 1:1.5 to about 1.5:1; from about 1:1.3 to about 1.3:1 or from about 1:1.1 to about 1.1:11.

Active Agents

In certain embodiments, any of the following active agents can be used in the solid oral dosage form of the present invention: ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, anti-pyretics, anti-inflammatory agents, androgens, local and general anesthetics, anti-addictive agents, anti-androgens, anti-arrhythmic agents, anti-asthmatic agents, anti-cholinergic agents, anti-cholinesterase agents, anti-coagulants, anti-diabetic agents, anti-diarrheal agents, anti-diuretic, anti-emetic agents, pro-kinetic agents, anti-epileptic agents, anti-estrogens, anti-fungal agents, anti-hypertensive agents, anti-microbial agents, anti-migraine agents, anti-muscarinic agents, anti-neoplastic agents, anti-parasitic agents, anti-Parkinson's agents, anti-platelet agents, anti-progestins, anti-schizophrenia agents, anti-thyroid agents, anti-tussives, anti-viral agents, atypical antidepressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, cannabinoids, catecholamines and sympathomimetic drugs, cholinergic agonists, cholinesterase reactivators, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, 5-hydroxytryptamine antagonists, drugs for the treatment of hyperlipoproteinemia, hypnotics, sedatives, immunosupressive agents, laxatives, methylxanthines, moncamine oxidase inhibitors, neuromuscular blocking agents, organic nitrates, opioid agonists, opioid antagonists, pancreatic enzymes, phenothiazines, progestins, prostaglandins, agents for the treatment of psychiatric disorders, psychotropics, retinoids, sodium channel blockers, agents for spasticity and acute muscle spasms, succinimides, testosterones, thioxanthines, thrombolytic agents, thyroid agents, tricyclic antidepressants, inhibitors of tubular transport of organic compounds, drugs affecting uterine motility, vasodilators, vitamins, and mixtures thereof.

In certain embodiments, the active agent is a drug susceptible to abuse (e.g., an opioid agonist). In such embodiments, the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. In certain embodiments, the opioid agonist is selected from the group consisting of codeine, fentanyl, hydromorphone, hydrocodone, oxycodone, dihydrocodeine, dihydromorphine, morphine, tapentadol, tramadol, oxymorphone, pharmaceutically acceptable salts thereof, and mixtures thereof.

In certain embodiments, the opioid agonist is oxycodone or a pharmaceutically acceptable salt thereof (e.g., oxycodone hydrochloride) in an amount, e.g., from about 2.5 mg to about 320 mg, or in an amount of about 2.5 mg, 5 mg, 7.5 mg, 10 mg, 15 mg, 20 mg, 25 mg, 30 mg, 40 mg, 60 mg, 80 mg, 120 mg, 160 mg or 320 mg.

In certain embodiments of the present invention, wherein the active agent is oxycodone hydrochloride, the oxycodone hydrochloride has a 14-hydroxycodeinone level of less than about 25 ppm, less than about 15 ppm, less than about 10 ppm, less than about 5 ppm, less than about 2 ppm, less than about 1 ppm, less than about 0.5 ppm or less than about 0.25 ppm.

WO 2005/097801 A1, U.S. Pat. No. 7,129,248 B2 and US 2006/0173029 A1, all of which are hereby incorporated by reference, describe a process for preparing oxycodone hydrochloride having reduced levels of 14-hydroxycodeinone.

In certain embodiments, the opioid agonist is morphine or a pharmaceutically acceptable salt thereof (e.g., morphine sulfate) in an amount, e.g., of from about 15 mg to about 200 mg, or in an amount of about 10 mg, 15 mg, 20 mg, 25 mg, 30 mg, 40 mg, 50 mg, 60 mg, 80 mg, 100 mg, 120 mg, 150 mg or 200 mg.

In embodiments in which the opioid analgesic comprises hydrocodone, dosage forms may include analgesic doses from about 2 mg to about 50 mg of hydrocodone bitartrate. In embodiments in which the opioid analgesic comprises hydromorphone the dosage form may include from about 2 mg to about 64 mg hydromorphone hydrochloride.

The solid oral dosage forms of the present invention can provide a controlled release of the active agent. Certain embodiments can also provide a first portion of the active agent for immediate release and a second portion of the active agent for controlled release. For example, an immediate release portion of the drug can be layered over the particles of the dosage form or can be included in additional tablet excipients of which the particles are embedded.

In certain embodiments, the solid oral dosage form of the present invention comprises an active agent that is an opioid antagonist (with or without an opioid agonist). In such embodiments, the opioid antagonist is selected from the group consisting of amiphenazole, naltrexone, methylnaltrexone, naloxone, nalbuphine, nalorphine, nalorphine dinicotinate, nalmefene, nadide, levallorphan, cyclozocine, pharmaceutically acceptable salts thereof and mixtures thereof.

In certain embodiments, the solid oral dosage form of the present invention comprises an active agent that is a non-opioid analgesic. In such embodiments, the non-opioid analgesic is a non-steroidal anti-inflammatory agent selected from the group consisting of aspirin, celecoxib, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof and mixtures thereof.

In other embodiments, the present invention is directed to the dosage forms disclosed herein utilizing active agents such as benzodiazepines, barbiturates or amphetamines, their antagonists, or combinations thereof.

Benzodiazepines to be used in the present invention may be selected from alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, and pharmaceutically acceptable salts, hydrates, and solvates and mixtures thereof. Benzodiazepine antagonists that can be used in the present invention include, but are not limited to, flumazenil and pharmaceutically acceptable salts, hydrates, and solvates.

Barbiturates to be used in the present invention include, but are not limited to, amobarbital, aprobarbotal, butabarbital, butalbital, methohexital, mephobarbital, metharbital, pentobarbital, phenobarbital, secobarbital and pharmaceutically acceptable salts, hydrates, and solvates mixtures thereof. Barbiturate antagonists that can be used in the present invention include, but are not limited to, amphetamines and pharmaceutically acceptable salts, hydrates, and solvates.

Stimulants to be used in the present invention include, but are not limited to, amphetamines, such as amphetamine, dextroamphetamine resin complex, dextroamphetamine, methamphetamine, methylphenidate and pharmaceutically acceptable salts, hydrates, and solvates and mixtures thereof. Stimulant antagonists that can be used in the present invention include, but are not limited to, benzodiazepines, and pharmaceutically acceptable salts, hydrates, and solvates as described herein.

Certain embodiments contain more than one active agent. For example, the dosage forms disclosed herein can contain both an opioid agonist and a non-opioid analgesic. In particular embodiments, the non-opioid analgesic is acetaminophen or a non-steroidal anti-inflammatory agent (e.g., ibuprofen, aspirin or diclofenac) and the opioid agonist is oxycodone, hydrocodone or pharmaceutically acceptable salts thereof (e.g., oxycodone hydrochloride or hydrocodone bitratrate).

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Example 1A

Preparation of Oxycodone-Eudragit® NE Granules

Oxycodone HCl-Eudragit® NE granules were prepared with various additives to determine the effect the additives have on the adherence of neutral acrylic polymer (Eudragit® NE) (NE) to Oxycodone HCl. In this and all of the following Examples, the neutral acrylic polymer used is Eudragit® NE 40 D.

Oxycodone HCl was granulated with low viscosity hydroxypropylmethylcellulose (HPMC E5), Nonoxynol 9 or carbomer (Carbopol® 71G) in a high shear granulator to form seed granules. These Oxycodone HCl seed granules were screened then further granulated/layered with Eudragit® NE dispersion containing methylcellulose having a viscosity of 1,500 cPs in 2% solution (MC A15C) in a rotor-granulator, followed by drying in the rotor-granulator. The ratios of the ingredients (by weight) are shown in Table 1A below.

TABLE 1A

| Components | % | | | |
|---|---|---|---|---|
| Oxycodone HCl | 5.8 | 5.5 | 5.3 | 5.5 |
| Eudragit ® NE | 93.7 | 93.7 | 93.7 | 93.7 |
| Methyl Cellulose A15C | 0.5 | 0.5 | 0.5 | 0.5 |
| HPMC E5 | 0 | 0.3 | 0 | 0 |
| Nonoxynol 9 | 0 | 0 | 0.5 | 0 |
| Carbopol ® 71G | 0 | 0 | 0 | 0.3 |

The granules were then tested for dissolution after tampering, and the results for Oxycodone-Eudragit® NE granules with no additives, Oxycodone-Eudragit® NE granules with HPMC E5, Oxycodone-Eudragit® NE granules with Nonoxynol 9 and Oxycodone-Eudragit® NE granules with Carbopol® 71G are shown in FIGS. 1A, 1B, 1C and 1D, respectively.

Example 1B

Preparation of Oxycodone-NE Granules with Lactose

Since the Oxycodone HCl-Eudragit® NE granules with Carbopol® 71G exhibited the best tamper resistance, Oxycodone-NE granules with Carbopol® 71G were prepared in accordance with Example 1A, with varying amounts of Oxycodone HCl, methylcellulose having a viscosity of 40,000 cPs in 2% solution (MC A40M), Eudragit® NE and lactose monohydrate to determine the effects on dissolution in SGF. The compositions of components (weight %) of the various formulations prepared are shown in Table 1B below.

TABLE 1B

| | Components | % | % | % |
|---|---|---|---|---|
| Internal Core | Oxycodone HCl | 5.9 | 5.8 | 44.2 |
| | Carbopol ® 71G | 0.3 | 2.1 | 2.2 |
| | MC A40M | 37.0 | 36.3 | 0 |
| NE Layer | Eudragit ® NE | 54.1 | 51.9 | 48.7 |
| | Lactose monohydrate | 2.7 | 3.9 | 4.9 |

Figure 2:
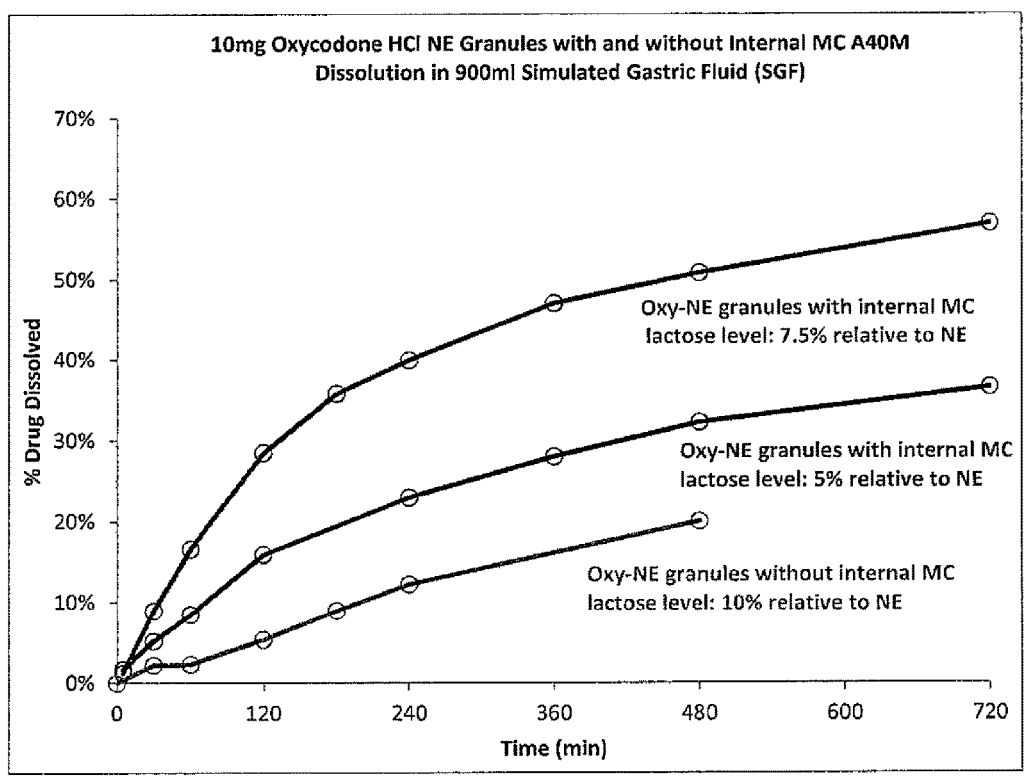
FIG. 2 depicts a graphical representation of the dissolution of the formulations of Example 1B in SGF.

Dissolution was then tested, and the results are shown in FIG. 2. As shown, in the absence of internal MC A40M, higher levels of lactose (10% relative to NE) were not able to increase dissolution rate from Oxycodone-NE granules. However, the presence of internal MC A40M had an enhancing effect on the dissolution rate of the Oxycodone-NE granules.

Example 1C

Oxycodone HCl:Eudragit® NE Ratio

Oxycodone HCl-Eudragit® NE granules were prepared in accordance with Example 1A, with varying amounts of components to determine the relationship between particle size and resistance to milling. Particle sizes greater than 600 µm and less than 600 µm were prepared. The compositions of components (weight %) in the various formulations prepared are shown in Table 1C below.

TABLE 1C

|  | Components | Particle >600 μm ~80% of all particles % | Particle <600 μm ~20% of all particles % |
|---|---|---|---|
| Internal core | Oxycodone HCl | 5.9 | 1.5 |
|  | Carbopol ® 71G | 0.3 | 0.1 |
|  | MC A40M | 37.0 | 9.5 |
| NE layer | Eudragit ® NE | 54.1 | 84.7 |
|  | Lactose monohydrate | 2.7 | 4.2 |

Figure 3A:
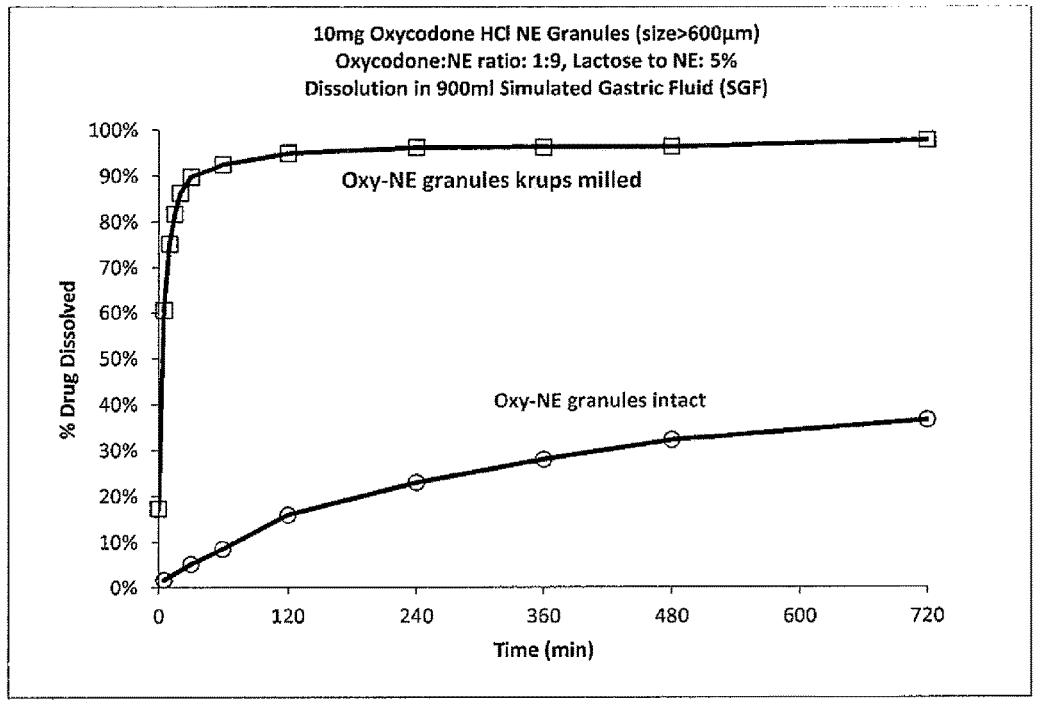
FIG. 3A depicts a graphical representation of the dissolution of the formulation of Example 1C with granules>600 μm in SGF.
Figure 3B:
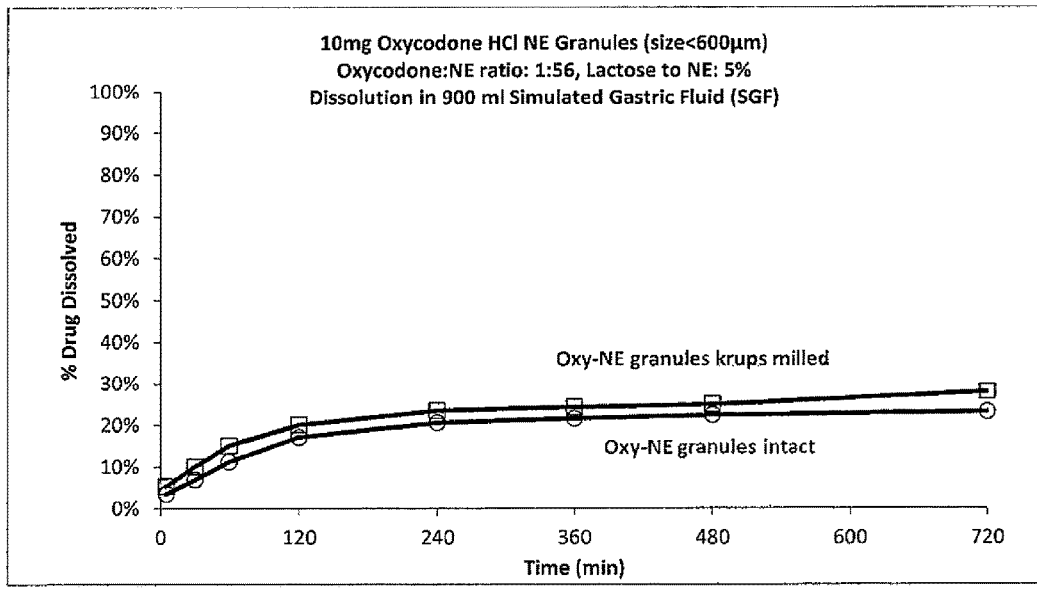
FIG. 3B depicts a graphical representation of the dissolution of the formulation of Example 1C with granules<600 μm in SGF.

Dissolution was then tested, and the results for granules greater than 600 μm and less than 600 μm are shown in FIGS. 3A and 3B, respectively. As shown, the smaller sized granules had higher Eudragit® NE loading, and better resistance to milling.

Next, the formulations were varied to test the effects of the amounts of Carbopol® 71G and lactose monohydrate on the formulation. The compositions of components (weight %) in the various formulations prepared are shown in Table 1D below.

TABLE 1D

|  | Components | Particle >600 μm ~52% of all particles % | Particle <600 μm ~48% of all particles % |
|---|---|---|---|
| Internal core | Oxycodone HCl | 5.8 | 3.4 |
|  | Carbopol ® 71G | 2.1 | 1.3 |
|  | MC A40M | 36.3 | 21.6 |
| NE layer | Eudragit ® NE | 51.9 | 68.6 |
|  | Lactose monohydrate | 3.9 | 5.1 |

Figure 4A:
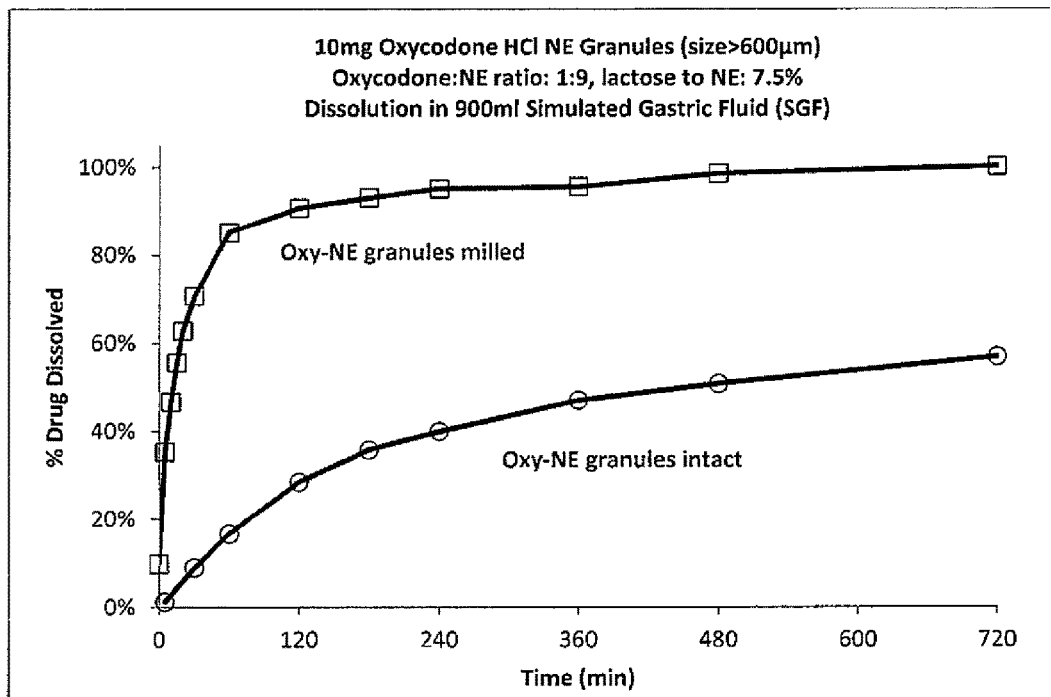
FIG. 4A depicts a graphical representation of the dissolution of the formulation of Example 1C with granules>600 μm with Carbopol® 71G in SGF.
Figure 4B:
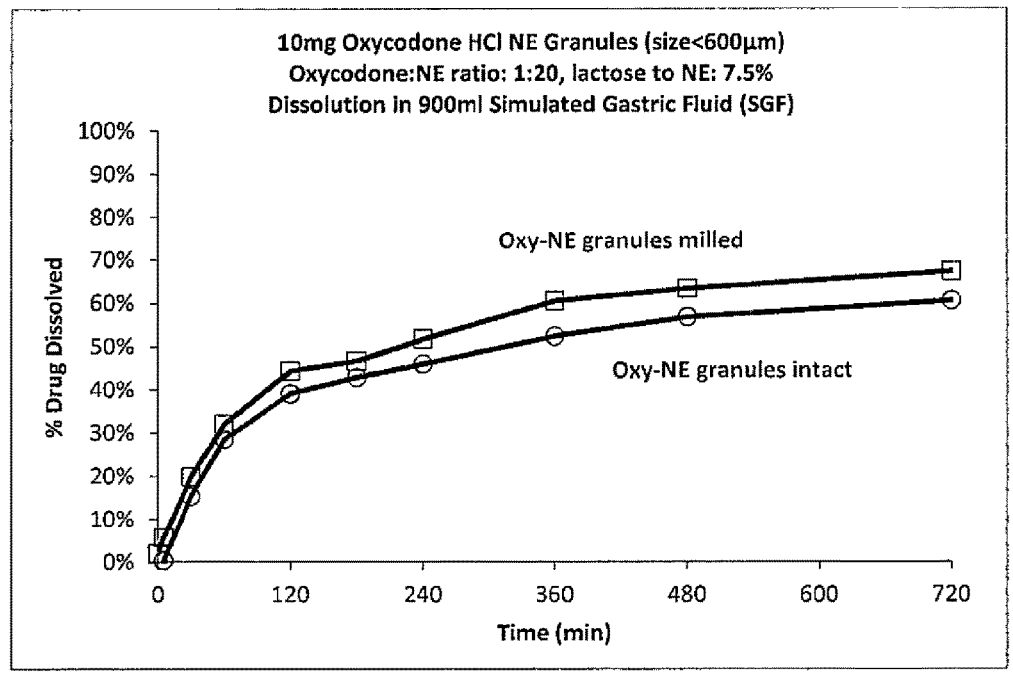
FIG. 4B depicts a graphical representation of the dissolution of the formulation of Example 1C with granules<600 μm with Carbopol® 71G in SGF.

Dissolutions were then tested, and the results for granules greater than 600 μm and less than 600 μm are shown in FIGS. 4A and 4B, respectively. As shown, increasing levels of Carbopol® 71G and lactose monohydrate improved granule particle size and Eudragit® NE coating uniformity. Similar to Example 1C, the smaller sized granules had higher Eudragit® NE loading, and better resistance to milling.

Figure 5:
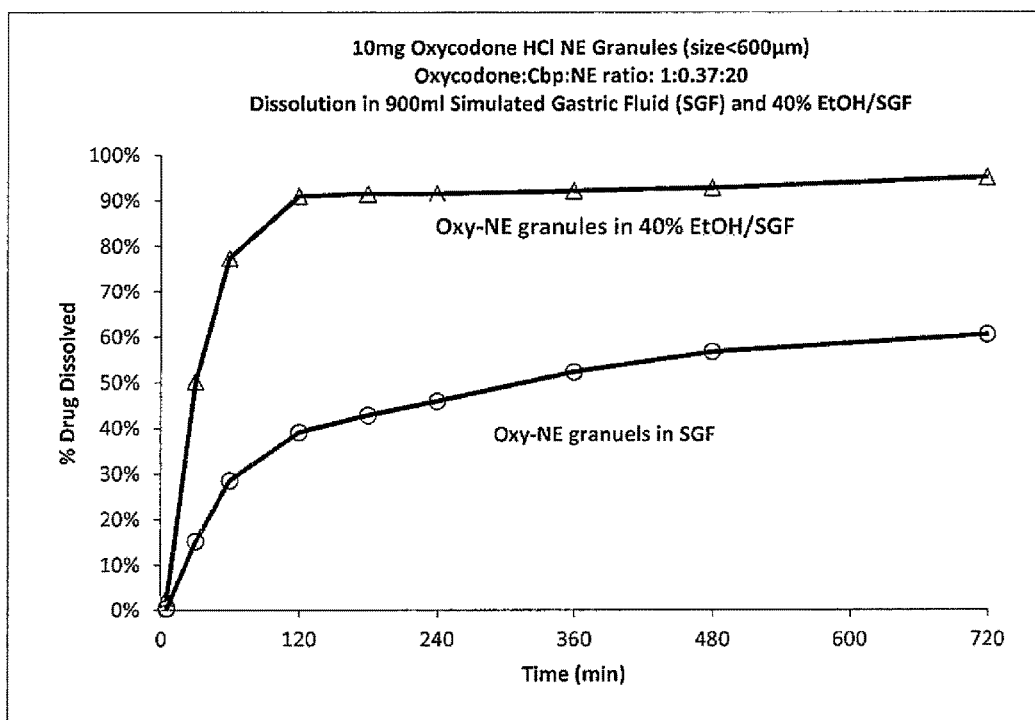
FIG. 5 is a graphical depiction of the dissolution of the formulation of Example 1C with Carbopol® 71G in 40% EtOH/SGF.

The Oxycodone HCl-Eudragit® NE granules with Carbopol® 71G having a particle size of less than 600 μm were then tested for alcohol resistance in 40% EtOH/SGF. The results are shown in FIG. 5. As shown, the Oxycodone HCl-Eudragit® granules were not alcohol resistant.

Example 1D

Film Coating

In an attempt to improve alcohol resistance, the Oxycodone HCl-Eudragit® NE granules with Carbopol® 71G of Example 1C were coated with an external layer of methylcellulose (MC A15LV). The compositions of the components (weight %) of the formulation are shown in Table 1E below.

TABLE 1E

|  | Components | % |
|---|---|---|
| Internal | Oxycodone HCl | 3.2 |
|  | Carbopol ® 71G | 1.2 |
|  | MC A40M | 20.4 |
| NE | Eudragit ® NE | 65.5 |

TABLE 1E-continued

|  | Components | % |
|---|---|---|
| Layer | Lactose monohydrate | 4.9 |
| External Layer | MC A 15LV | 4.8 |

Figure 6:
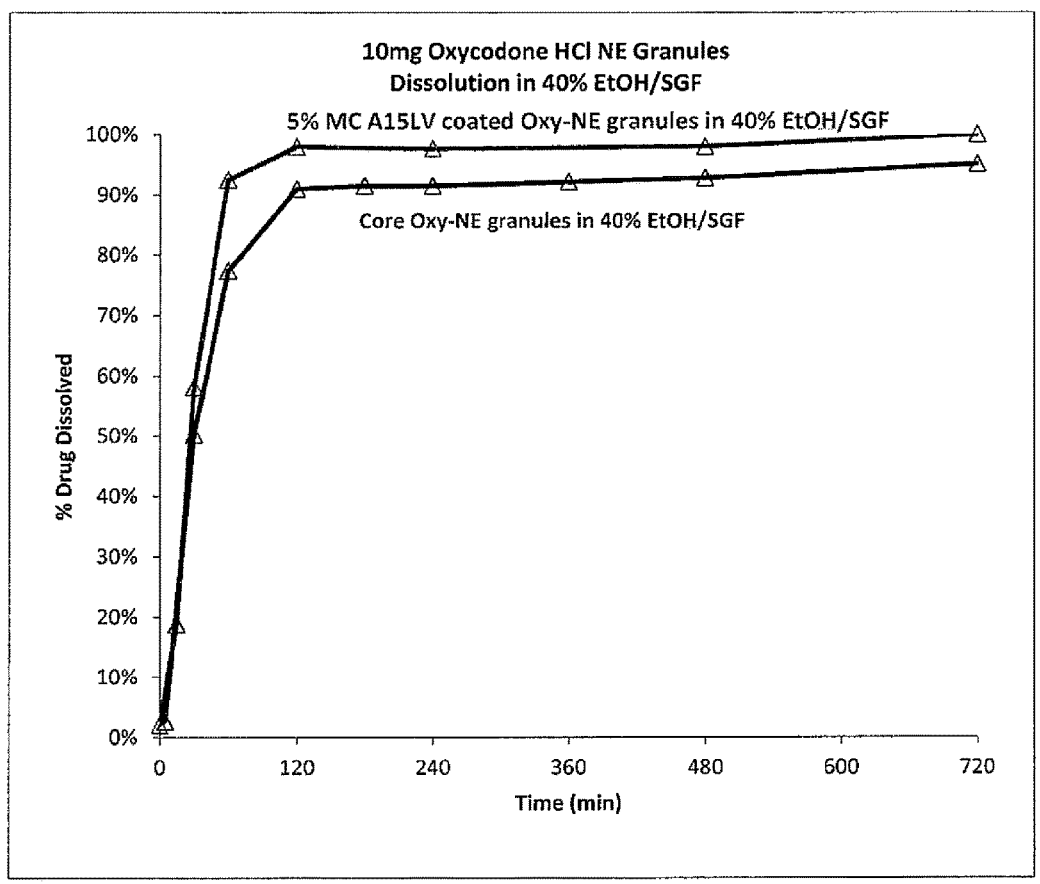
FIG. 6 is a graphical depiction of the dissolution of the formulation of Example 1D in 40% EtOH/SGF.

This formulation was then tested for alcohol resistance and the data compared with the formulation without the external MC layer, as shown in FIG. 6. As shown, the addition of the 4.8% film coating of MC A15LV did not improve alcohol resistance.

Example 1E

Granulation with External Excipients

The formulation was then modified to replace the external coat of MC A15LV by wet granulation with extra-granular MCA40M (granulated with water). The compositions (weight %) of formulations, as compared to the formulation without the extra-granular MC A40M, are shown in Table 1F below.

TABLE 1F

|  | Components | Core Oxycodone-NE % | Low Ext. MCA40M % | High Ext. MCA40M % |
|---|---|---|---|---|
| Internal | Oxycodone HCl | 3.4 | 1.7 | 1.1 |
|  | Carbopol ® 71G | 1.3 | 0.6 | 0.4 |
|  | MC A40M | 21.6 | 10.8 | 7.2 |
| NE Layer | Eudragit ® NE | 68.6 | 34.6 | 23.1 |
|  | Lactose monohydrate | 5.1 | 2.6 | 1.7 |
| External Layer | MC A40M | 0 | 49.7 | 66.5 |

Figure 7:
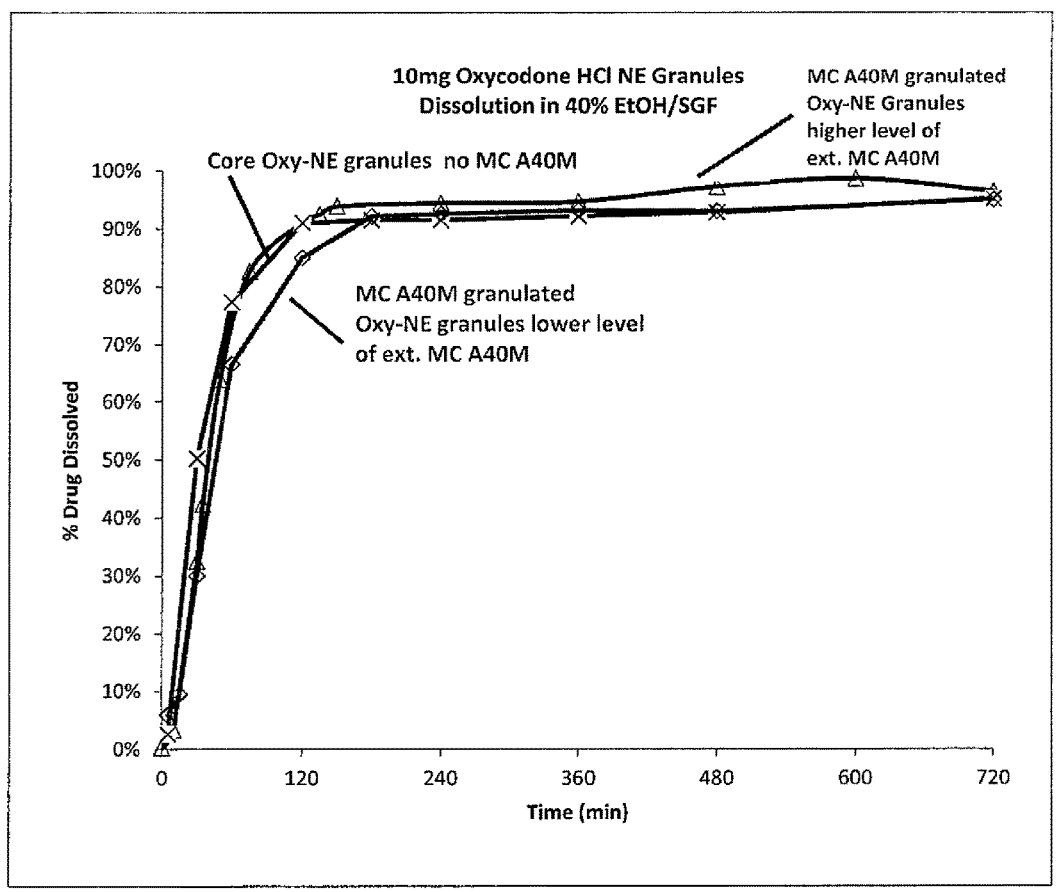
FIG. 7 is a graphical depiction of the dissolution of the formulation of Example 1E without Carbopol® 71G in the external layer in 40% EtOH/SGF.

The formulations with extra-granular MC A40M were then tested for alcohol resistance, and the results are shown in FIG. 7. As shown, there was no improvement on alcohol resistance.

Next, Carbopol® 71G was added to the extra-granular layer in the amounts (by weight) shown in Table 1G below.

TABLE 1G

|  | Components | Core Oxycodone-NE % | External MC A40M granulated without Carbopol ® 71G % | External MC A40M granulated with Carbopol ® 71G % |
|---|---|---|---|---|
| Internal | Oxycodone HCl | 3.4 | 1.7 | 2.6 |
|  | Carbopol ® 71G | 1.3 | 0.6 | 0.9 |
|  | MC A40M | 21.6 | 10.8 | 16.3 |
| NE Layer | Eudragit ® NE | 68.6 | 34.6 | 52.4 |
|  | Lactose monohydrate | 5.1 | 2.6 | 3.9 |
| External Layer | MCA40M | 0 | 49.7 | 19.0 |
|  | Carbopol ® 71G | 0 | 0 | 4.9 |

Figure 8:
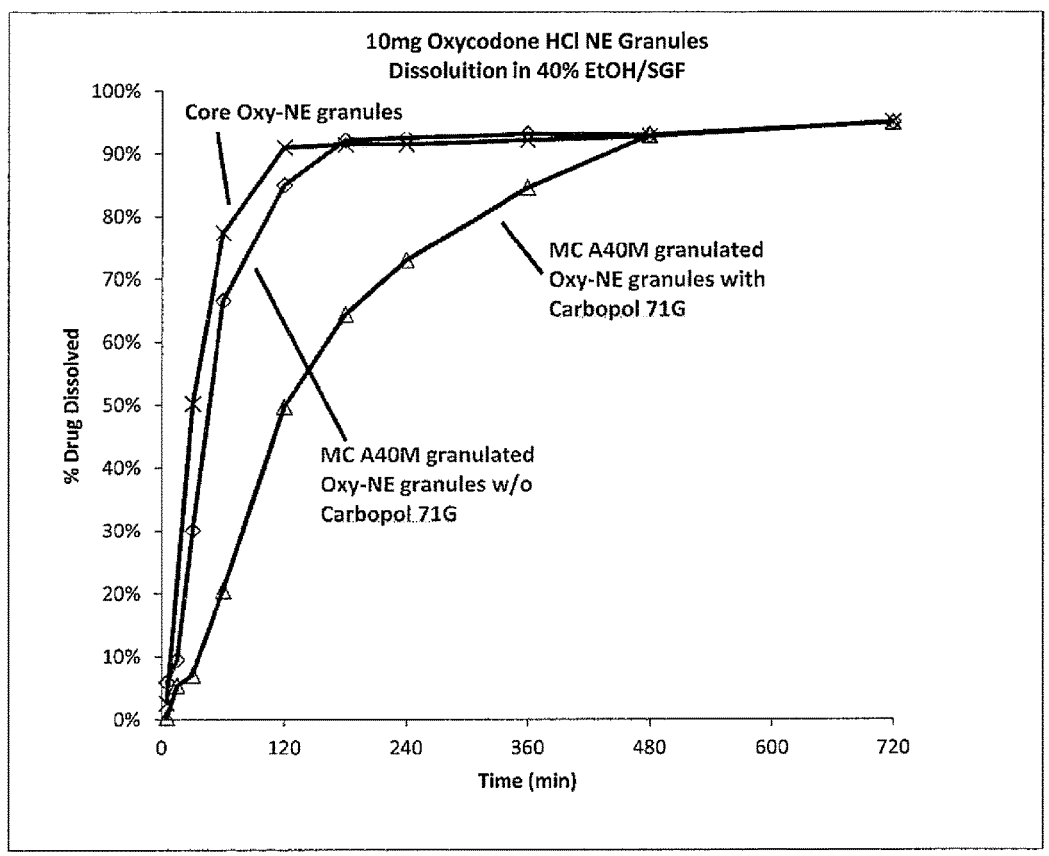
FIG. 8 is a graphical depiction of the dissolution of the formulation of Example 1E with Carbopol® 71G in the external layer in 40% EtOH/SGF.

Oxycodone HCl-Eudragit® NE granules were prepared with various levels of additives to determine the effect the additives have on the adherence of Eudragit® NE to MC A40M and consequently on alcohol resistance The extra-granular MCA40M/Carbopol® 71G formulation was then tested for alcohol resistance, and the results are shown in FIG. 8. As shown, the granulation of external MC A40M with Carbopol® 71G solution as a binder improved binding and adhesion of the external MC A40M to the Eudragit® NE, thereby improving the alcohol resistance.

To determine the effect of the amount of Carbopol® 71G on alcohol resistance, the amount of Carbopol® 71G was doubled, as shown in Table 1H below.

TABLE 1H

| | Components | Core Oxycodone-NE granules % | Oxycodone-NE-MC (lower level of ext. MCA40M) % | Oxycodone-NE-MC (higher level of ext. MCA40M) % |
|---|---|---|---|---|
| Internal | Oxycodone HCl | 3.4 | 2.6 | 2.1 |
| | Carbopol ® 71G | 1.3 | 0.9 | 0.8 |
| | MC A40M | 21.6 | 16.3 | 13.2 |
| NE Layer | Eudragit ® NE | 68.6 | 52.4 | 42.2 |
| | Lactose | 5.1 | 3.9 | 3.2 |
| External Layer | MCA40M | 0 | 19.0 | 30.7 |
| | Carbopol ® 71G | 0 | 4.9 | 7.8 |

Figure 9:
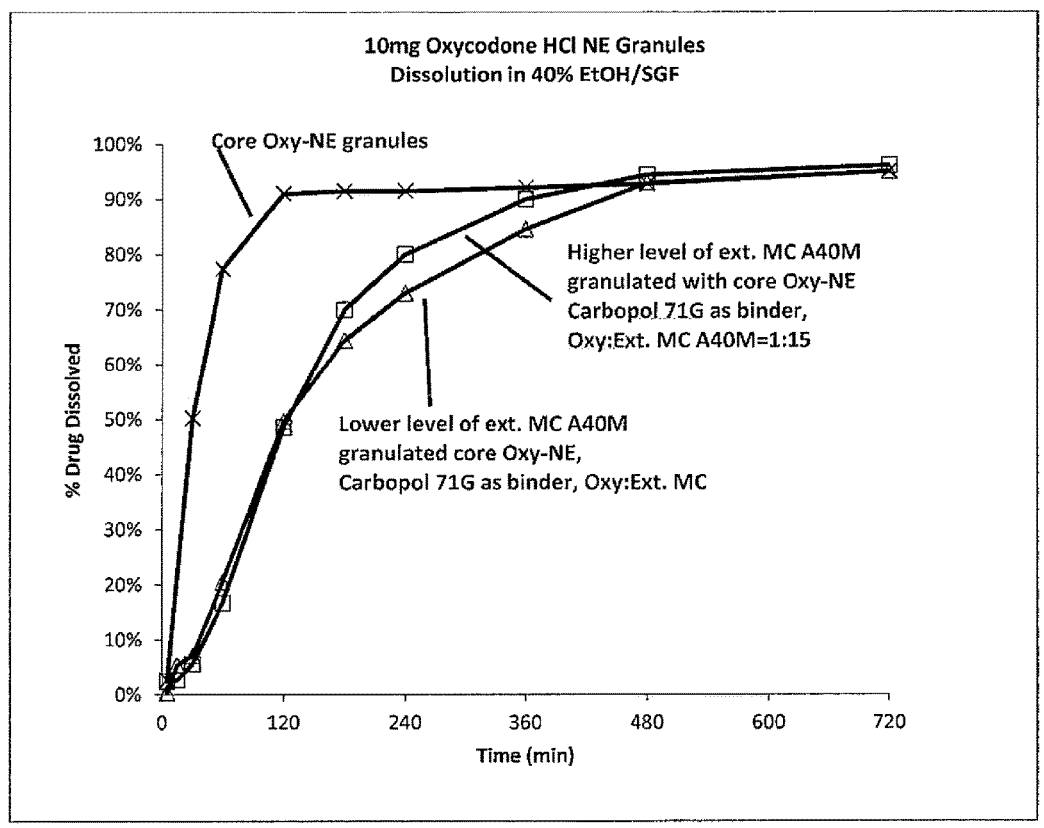
FIG. 9 is a graphical depiction of the dissolution of the formulation of Example 1E with additional Carbopol® 71G in the external layer in 40% EtOH/SGF.

The extra-granular MCA40M/Carbopol® 71G formulation was then tested for alcohol resistance, and the results are shown in FIG. 9. As shown, increased amount of Carbopol® 71G did not improve alcohol resistance.

Figure 10:
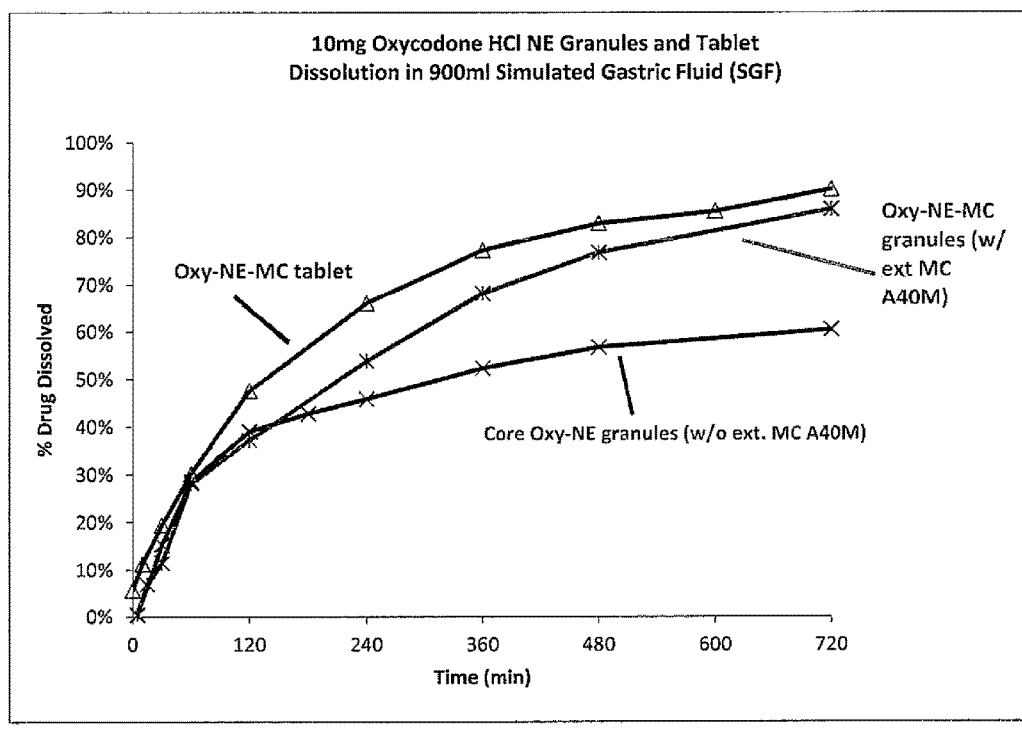
FIG. 10 is a graphical depiction of the dissolution of the formulation of Example 1E in SGF.

The dissolution of 4.9% Carbopol® 71G (external layer) formulation was then tested in 900 ml SGF, and the results are shown in FIG. 10. As shown, the external layer of MC/Carbopol® 71G also helps to increase the dissolution in SGF.

Figure 11:
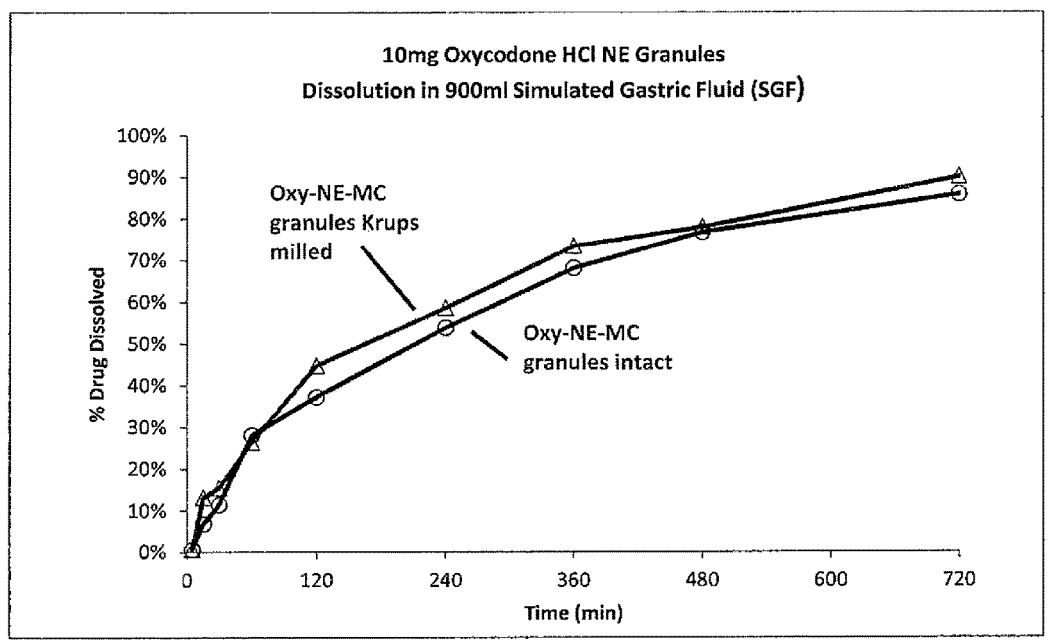
FIG. 11 is a graphical depiction of the dissolution of the formulation of Example 1E after milling in SGF.

The formulation was then tested for resistance to milling, and the results are shown in FIG. 11. As shown, the external layer of MC/Carbopol® 71G did not compromise the resistance of the granules to milling.

Example 2

10 mg Oxycodone HCl-Eudragit® NE Tablet Preparation
Tablet formulations were prepared as follows:

Internal Core—Stage 1

Equipment
Vector GMX Micro High-Shear granulator
Glatt® Fluid Bed Dryer—Model Versa Glatt
Comil® Comminuting Mill
Stainless Steel Screens—US Std. #18, #30
  Procedure
  1. A 4% w/w binder solution of Carbopol® 71G in 0.1 N HCl was prepared.
  2. Carbopol® 71G in the internal core was added in two parts. 60% of the Carbopol® 71G was added dry with Oxycodone HCl and methyl cellulose (MCA40M) in the granulator. Remainder 40% Carbopol® 71G was added as the binder solution (Step 1).
  3. The ingredients for the internal core—oxycodone HCl, methyl cellulose A40M (MC) and Carbopol® 71G were charged into the bowl of high-shear granulator (impeller speed 300 rpm, chopper speed 300 rpm) and dry mixed for 1 minute.
  4. The mixture from step 3 was granulated with Carbopol® 71G binder solution (from step 1) which was sprayed at 20 g/min
  5. If required, additional water was sprayed during granulation to obtain a cohesive free flowing mass.
  6. The wet granulations were milled through Comil® fitted with mesh #18 (1000 micron opening) screen.
  7. The wet milled granulations were dried in a fluid bed dryer at inlet temperature of 45° C., and an air volume adjusted to fluidize the bed. The moisture content of the dried granulations was <5%.
  8. The dried granulations were milled through Comil® fitted with mesh #30 (600 micron opening) screen.

Eudragit® NE Layer—Stage 2

Equipment
Vector VFC-Lab3 Ho-Coater with GXR-35 rotor—also called Rotor-granulator
Stainless Steel Screen—US Std. #30
Hotpack Tray Dryer
  Procedure
  1. Binder solution was prepared by mixing Eudragit® NE dispersion (27.9% Eudragit® NE solids) and lactose monohydrate (2.1%) to obtain total solids content of 30% w/w in the dispersion.
  2. The milled internal core granulations from Step 8/stage 1 were charged into the chamber of the rotor-granulator.
  3. The rotor was operated at plate speed=300 rpm, slit airflow=8 cfm, and inlet/slit temperature=25° C.
  4. Water was sprayed at a rate of 3.5 g/min until product temperature was below 16° C.
  5. When the product temperature was less than 16° C., Eudragit® NE-Lactose monohydrate dispersion spray was begun at 3.5 g/min.
  6. The product temperature was monitored and controlled such that it stayed between 14-16° C. The product temperature was controlled by adjusting binder spray rate, slit airflow, and slit temperature.
  7. Granule samples were collected at various levels of Eudragit® NE loading for testing. The granule samples were screened through mesh #30 screen, cured in a tray dryer at 60° C. for 24 hours, and tested for drug release from intact and milled/crushed granules.
  8. The end point of Eudragit® NE-Lactose layering was determined by dissolution results from step 7, i.e. dissolution profiles in SGF from intact and milled/crushed granules were similar. When the end-point was reached, Eudragit® NE-Lactose dispersion spraying was stopped.
  9. The granules were dried in the rotor at 25° C. till a moisture content of less than 5% was obtained.
  10. The granules were discharged from the rotor and screened through sieve #30 (opening 600 microns).
  11. The granules which passed through sieve #30 were cured in a tray dryer at 60° C. for 24 hours.

External Layer—Stage 3

Equipment
Vector GMX Micro High-Shear granulator
Glatt® Fluid Bed Dryer—Model Versa Glatt
Comil® Comminuting Mill
Stainless Steel Screens—US Std. #18
  Procedure
  1. A 4% w/w binder solution of Carbopol® 71G in 0.1 N HCl was prepared.
  2. Carbopol® 71G in the external layer was added in two parts. 60% of the Carbopol® 71G was added dry with cured, screened granules from Step 11/stage 2 and methyl cellulose A40M (MC A40M) in the granulator. Remainder 40% of Carbopol® 71G was added as the binder solution (step 1).

3. The ingredients for the external layering—cured, screened granules from Step 11/stage 2, methyl cellulose A40M (MC A40M) and Carbopol® 71G were charged into the bowl of high-shear granulator (impeller speed 300 rpm, chopper speed 300 rpm) and dry mixed for 1 minute.
4. The mixture from step 3 was granulated with Carbopol® 71G binder solution (from step 1) which was sprayed at 20 g/min
5. If required, additional water was sprayed during granulation to obtain a cohesive free flowing mass.
6. The wet granulations were milled through Comil® fitted with mesh #18 (1000 micron opening) screen.
7. The wet milled granulations were dried in a fluid bed dryer at inlet temperature of 45° C., and an air volume adjusted to fluidize the bed. The moisture content of the dried granulations was less than 5%.
8. The dried granulations were milled through Comil® fitted with mesh #18 (1000 micron opening) screen, and compressed into tablets The compositions (weight %) of the components in the tablet formulation are shown in Table 2 below.

TABLE 2

|  | Components | % |
| --- | --- | --- |
| Internal | Oxycodone HCl | 2.6 |
| Core | Carbopol ® 71G | 0.9 |
|  | MC A40M | 16.3 |
| NE | Eudragit ® NE | 52.4 |
| Layer | Lactose monohydrate | 3.9 |
| External | MC A40M | 19.0 |
| Layer | Carbopol ® 71G | 4.9 |

Dissolution of the prepared tablets was performed as follows:
1. Apparatus USP Type 2, paddles, 50 rpm at 37° C.
2. Sampling time—every 30 minutes up to 720 minutes.
3. Media—900 ml simulated gastric fluid (SGF, pH 1.2), or Simulated gastric fluid+Ethanol (60:40 v/v)
4. Analytical method—UV analysis, Distek Fiber Optic Dissolution System (Distek Opt-Diss 405) at wavelength 280 nm, double wavelength correction.

Assay
1. Sample diluted with simulated gastric fluid (SGF, pH 1.2)
2. Analytical method—UV analysis, Distek Fiber Optic Dissolution System (Distek Opt-Diss 405) at wavelength 280 nm, double wavelength correction.

Milling
1. 1 dose was added to the chamber of Krups coffee mill and milled for 15 sec, switching off for 10 sec. This procedure was repeated 3 more times for a total milling time of 60 sec.
2. Dissolution testing of milled samples in SGF was performed as described in "Dissolution" above.

Crushing
1. 1 dose was added to a glass mortar and triturated/crushed with pestle continuously for 2 minutes.
2. Dissolution testing of crushed samples in SGF was performed as described in "Dissolution" above.

Figure 12A:
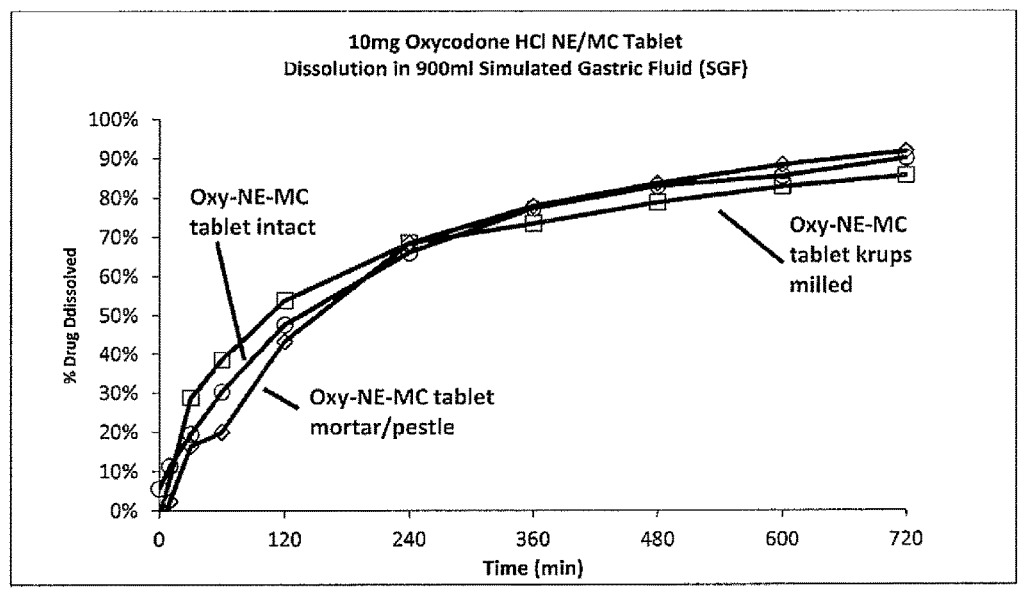
FIG. 12A is a graphical depiction of the dissolution of the tablet formulation of Example 2 intact and crushed and milled in SGF.
Figure 12B:
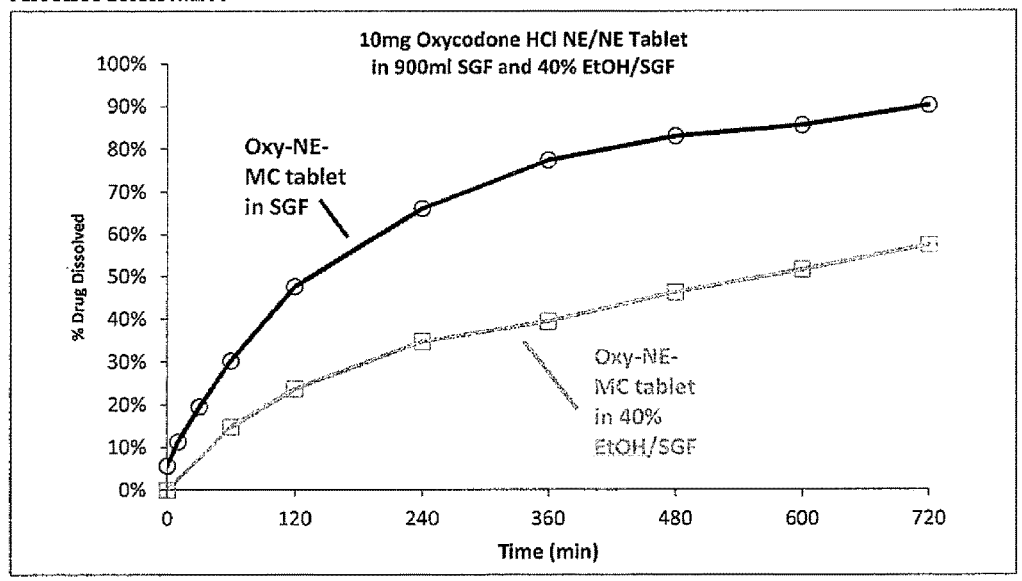
FIG. 12B is a graphical depiction of the dissolution of the tablet formulation of Example 2 intact and crushed and milled in alcohol/SGF.

The dissolution profiles of the tablet formulation, intact in SGF and crushed and milled in SGF are shown in FIG. 12A. The dissolution profiles of the intact tablet in alcohol/SGF and SGF, are shown in FIG. 12B.

Example 3

10 mg Oxycodone HCl-Eudragit® NE Tablet Small Volume Extraction & Syringability Studies The tablets of Example 2 were tested for extractability by small volume of various solvents at various temperatures. The studies were performed as follows:

Small Volume Extraction:
1. One dose of sample was milled in Krups coffee mill and transferred to a 60-ml glass vial with plastic closure.
2. 30 ml solvent was added to the vial and shaken in a water bath shaker at room and elevated temperatures (50° C. for organic solvents, 95° C. for aqueous solvents).
3. Aliquots of sample (5.0 mL) were removed at 10 and 60 min, diluted, filtered and assayed for drug content.

Figure 13A:
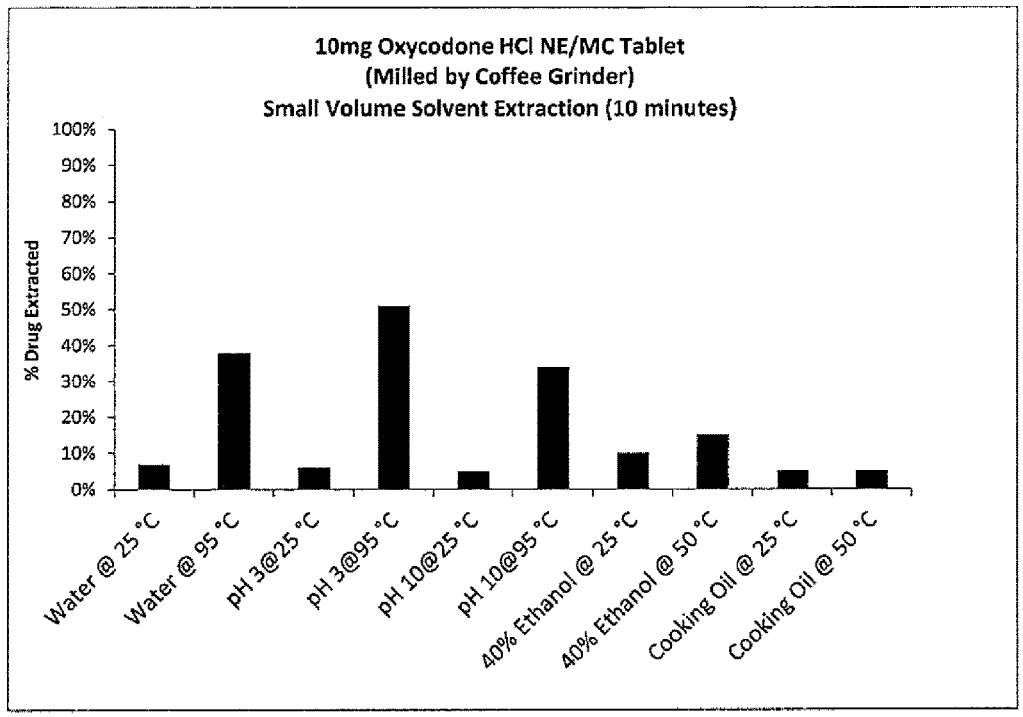
FIG. 13A is a graphical depiction of the extraction data from Example 3 after 10 minutes.
Figure 13B:
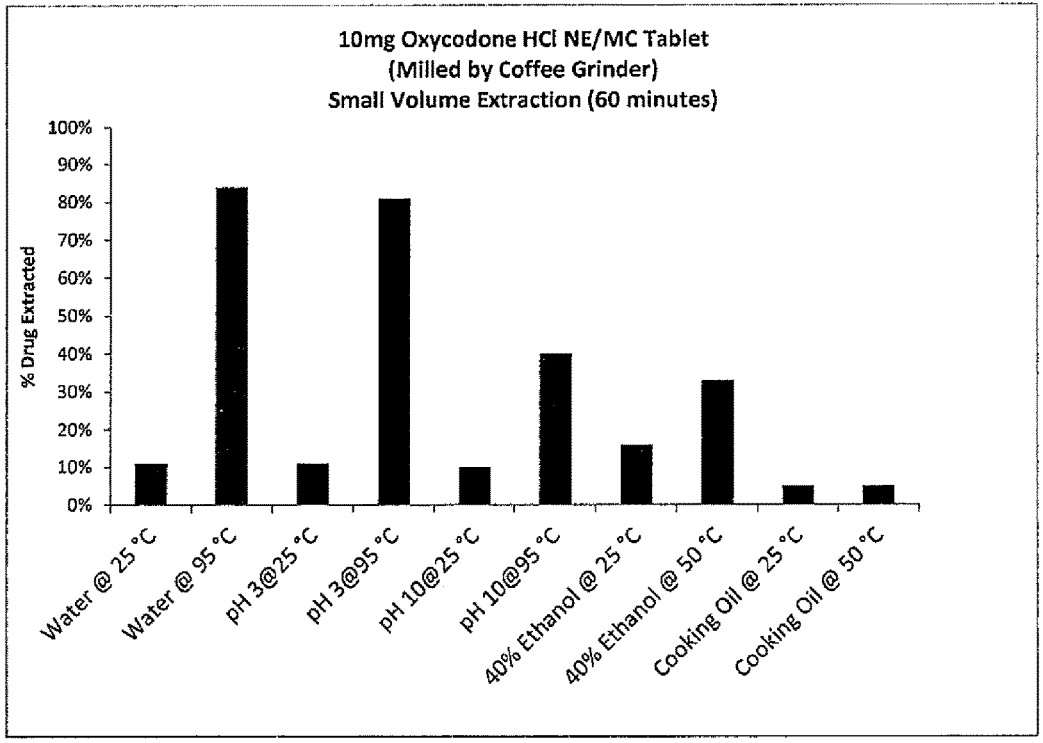
FIG. 13B is a graphical depiction of the extraction data from Example 3 after 60 minutes.

List of Extraction Solvents
Water, pH 3 buffer, pH 10 buffer, 40% Ethanol, Cooking Oil
The results after 10 minutes and 60 minutes are shown in FIGS. 13A and 13B, respectively.

Syringability:
Room Temperature Samples
1. One dose of sample was milled in Krups coffee mill, added to a vial with 5 or 10 ml distilled water and shaken by hand for 30 seconds.
2. Using a 18, 22, 25 or 27 gauge needle fitted on a 5 or 10 mL syringe, attempt was made to aspirate as much liquid as possible during a 5-minute time period. For the 10 minute time point—sample was allowed to stay in vial for 10 minutes before attempting to syringe.
3. The amount of drug extracted was assayed.

Heated Samples
1. One dose of sample was milled in Krups coffee mill, added to a vial with 5 ml distilled water. The sample was heated in vial with a butane lighter and shaken by hand for 30 seconds.
2. Using a 18, 22, 25 or 27 gauge needle fitted on a 5 or 10 mL syringe, attempt was made to aspirate as much liquid as possible during a 5-minute time period. For the 10 minute time point—sample was allowed to stay in vial for 10 minutes before attempting to syringe.
3. The amount of drug extracted was assayed.

Figure 14:
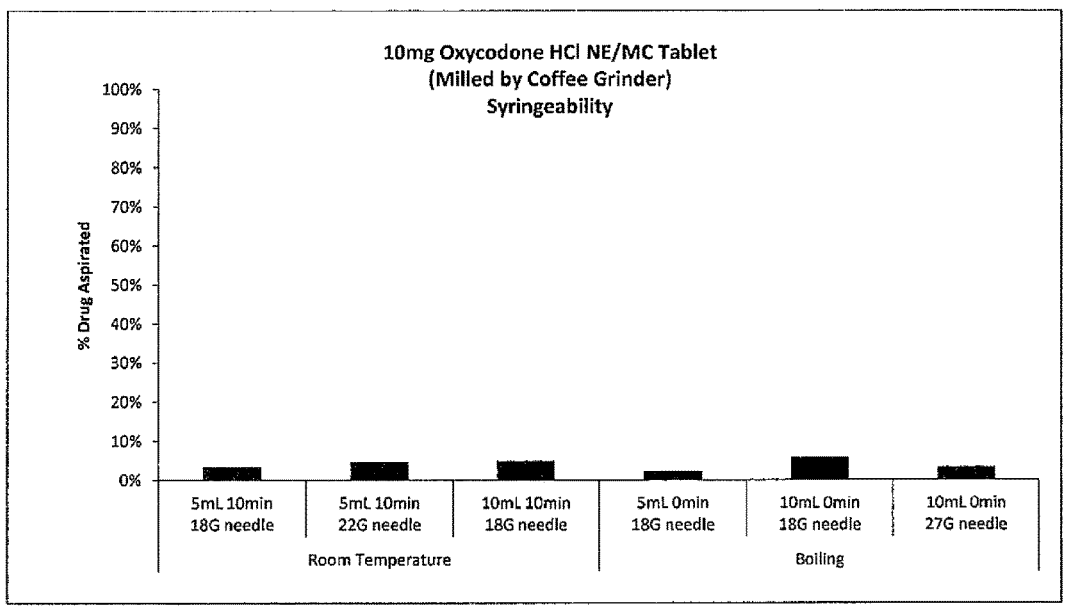
FIG. 14 is a graphical depiction of the syringability data from Example 3.

The results are shown in FIG. 14

Example 4A 15 mg Morphine Sulfate-Eudragit® NE Tablet Preparation

The subject tablet formulations were prepared with the composition (weight %) of components as shown in Table 4A below, using the equipment and procedures referred to in Example 2.

TABLE 4A

|  | Components | % (by weight) |
| --- | --- | --- |
| Internal | Morphine Sulfate | 4.2 |
| Core | Carbopol ® 71G | 1.1 |
|  | MC A40M | 17.1 |
| NE Layer | Eudragit ® NE | 48.7 |
|  | Lactose monohydrate | 3.7 |
| External | MC A40M | 21.5 |
| Layer | Carbopol ® 71G | 3.3 |
|  | Magnesium Stearate | 0.5 |

Figure 15A:
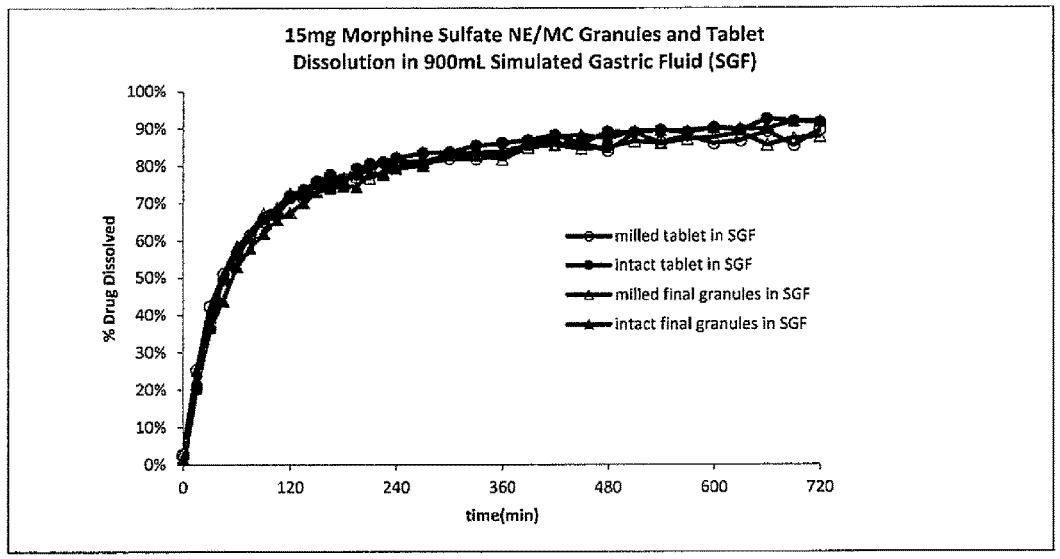
FIG. 15A is a graphical depiction of the dissolution of the tablet and granule formulation of Example 4A, milled and intact in SGF.
Figure 15B:
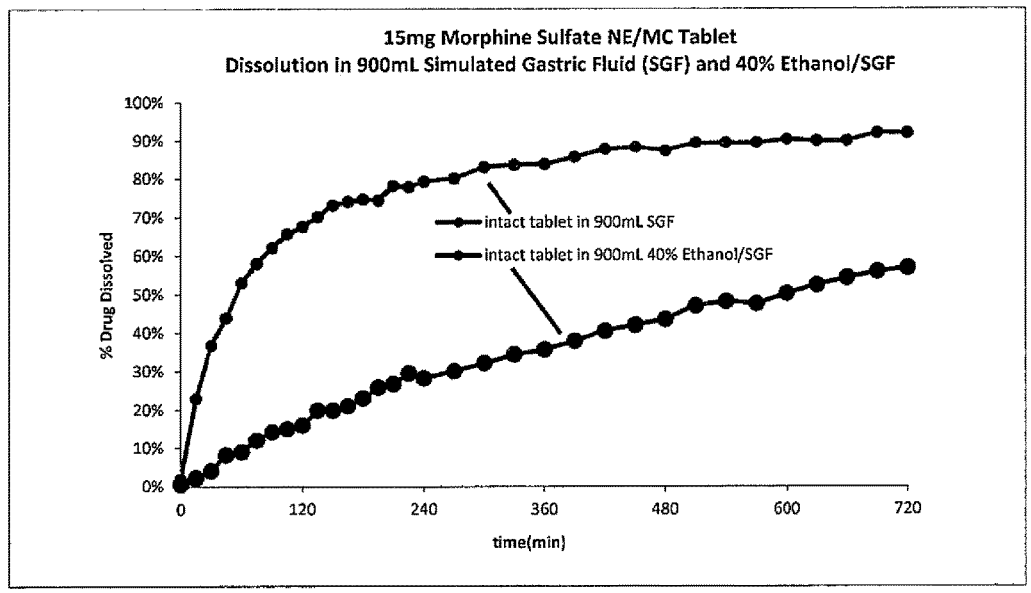
FIG. 15B is a graphical depiction of the dissolution of the tablet formulation of Example 4A, milled and intact in alcohol/SGF.

The tablet of Example 4A was subject to milling and dissolution according to the protocols in Example 2. The dissolution of a milled tablet formulation, an intact tablet formulation, milled final granules and intact final granules in 900 mL SGF is shown in FIG. 15A. The dissolution of an intact tablet formulation in 900 mL SGF and an intact tablet formulation in 900 mL of 40% alcohol/SGF is shown in FIG. 15B.

Example 4B 10 mg Oxycodone/5 mg Naloxone NE/MC Tablet Preparation

The subject tablet formulations were prepared with the composition (weight %) of components as shown in Table 4B below, using the equipment and procedures referred to in Example 2.

TABLE 4B

|  | Components | % (by weight) |
|---|---|---|
| Internal Core | Oxycodone HCl | 2.5 |
|  | Naloxone HCl | 1.4 |
|  | Carbopol ® 71G | 1.0 |
|  | MC A40M | 15.0 |
| NE Layer | Eudragit ® NE | 52.2 |
|  | Lactose monohydrate | 3.9 |
| External Layer | MC A40M | 18.9 |
|  | Carbopol ® 71G | 4.9 |
|  | Magnesium Stearate | 0.2 |

Figure 16:
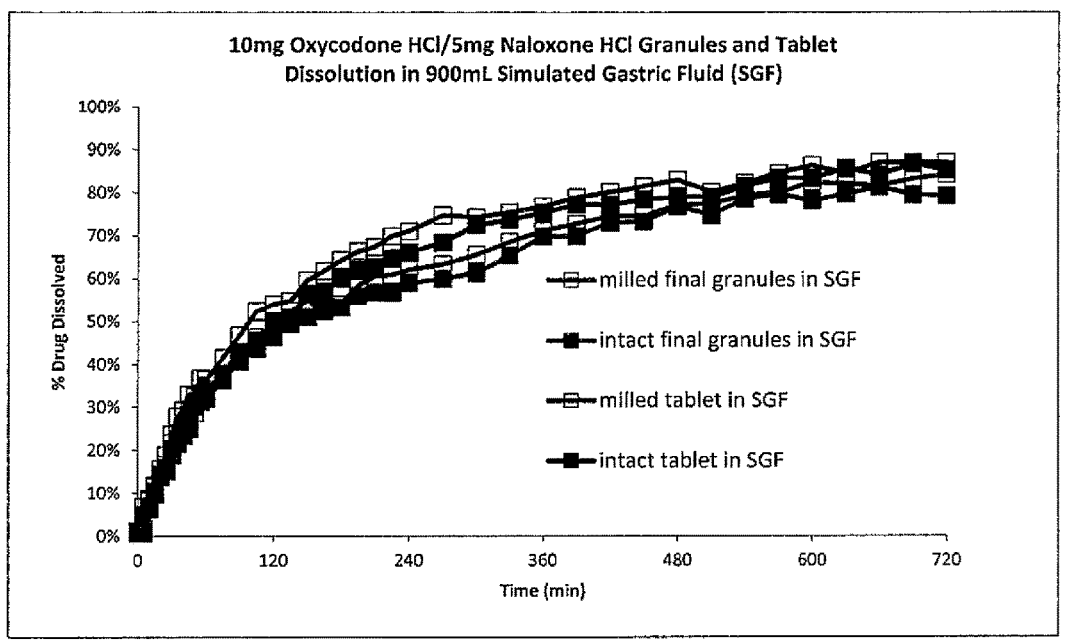
FIG. 16 is a graphical depiction of the dissolution of the tablet and granule formulation of Example 4B, milled and intact SGF.

The tablet of Example 4B was subject to milling and dissolution according to the protocols in Example 2. The dissolution of milled final granules, intact final granules, a milled tablet formulation and an intact tablet formulation in 900 mL SGF is shown in FIG. 16.

Example 4C

Preparation of 200 mg Morphine Sulfate-Eudragit® NE Granules with Different Internal Fillers The subject granules were prepared with the compositions of components (weight %) as shown in Table 4C below, using the equipment and procedures referred to in Example 2 (excluding Stage 3).

TABLE 4C

|  | Components | MC A40M As internal filler (low NE) % (by weight) | MC A40M as internal filler (higher NE) % (by weight) | Ac-Di-Sol as internal filler (low NE) % (by weight) | Ac-Di-Sol as internal filler (higher NE) % (by weight) |
|---|---|---|---|---|---|
| Internal Core | Morphine Sulfate | 25.1 | 15.8 | 27.7 | 16.5 |
|  | Carbopol ® 71G | 3.8 | 2.4 | 6.2 | 3.7 |
|  | MC A40M | 25.1 | 15.8 | 0 | 0 |
|  | Ac-Di-Sol | 0 | 0 | 13.9 | 8.3 |
| NE Layer | Eudragit ® NE | 42.7 | 61.5 | 48.5 | 66.5 |
|  | Lactose monohydrate | 3.2 | 4.6 | 3.6 | 5.0 |

Figure 17:
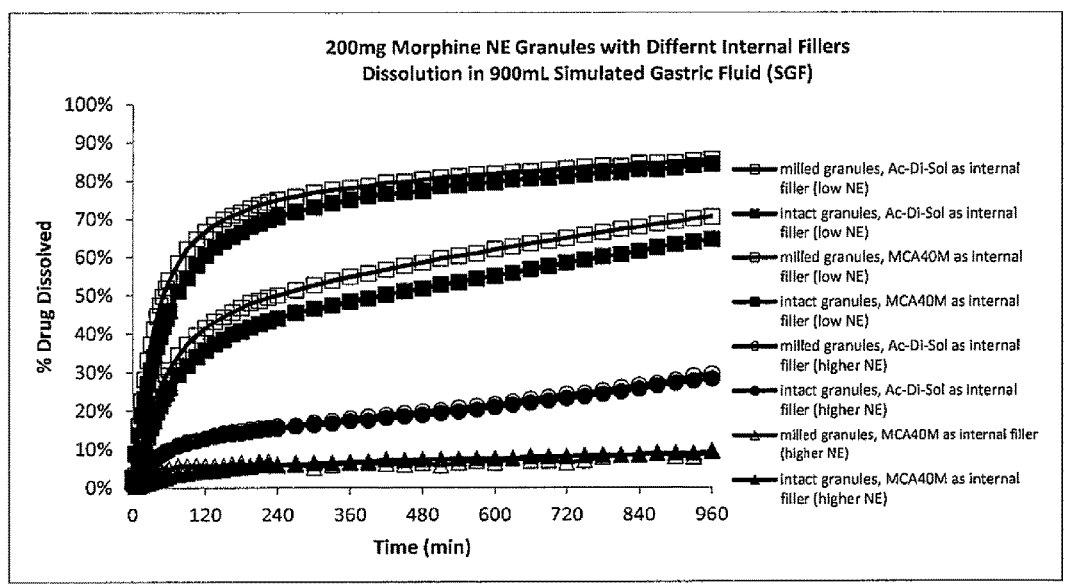
FIG. 17 is a graphical depiction of the dissolution of the granule formulation of Example 4C, milled and intact in SGF.

The granules of Example 4C were subjected to milling and dissolution according to the protocols in Example 2. The dissolution of milled and intact final granules with croscarmellose sodium (Ac-Di-Sol®) and low Eudragit® NE, milled and intact final granules with MC A40M and low Eudragit® NE, milled and intact final granules with Ac-Di-Sol and high Eudragit® NE, and milled and intact final granules with MC A40M and high Eudragit® NE in 900 mL SGF is shown in FIG. 17.

Figure 18A:
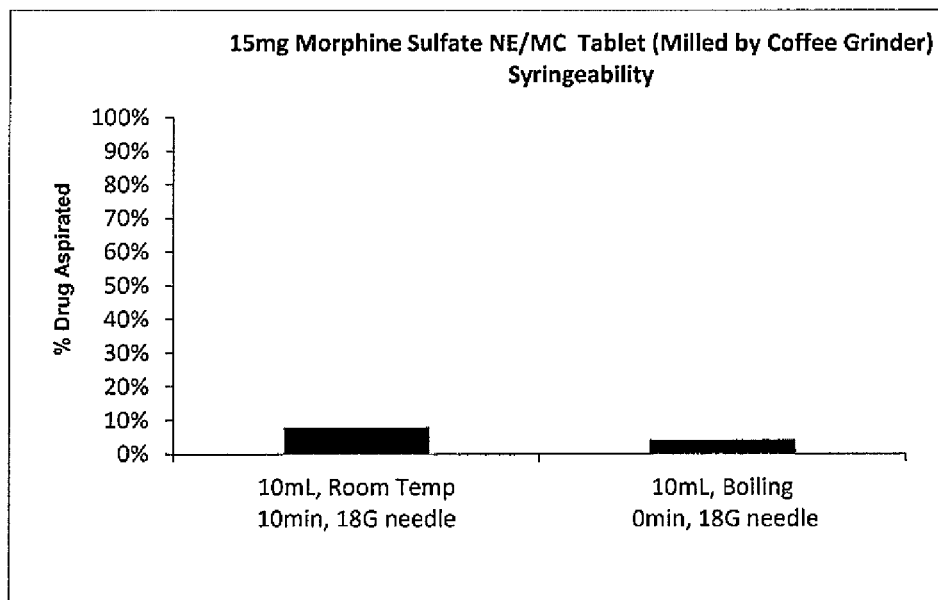
FIG. 18A is a graphical depiction of the syringability data from Example 5A.
Figure 18B:
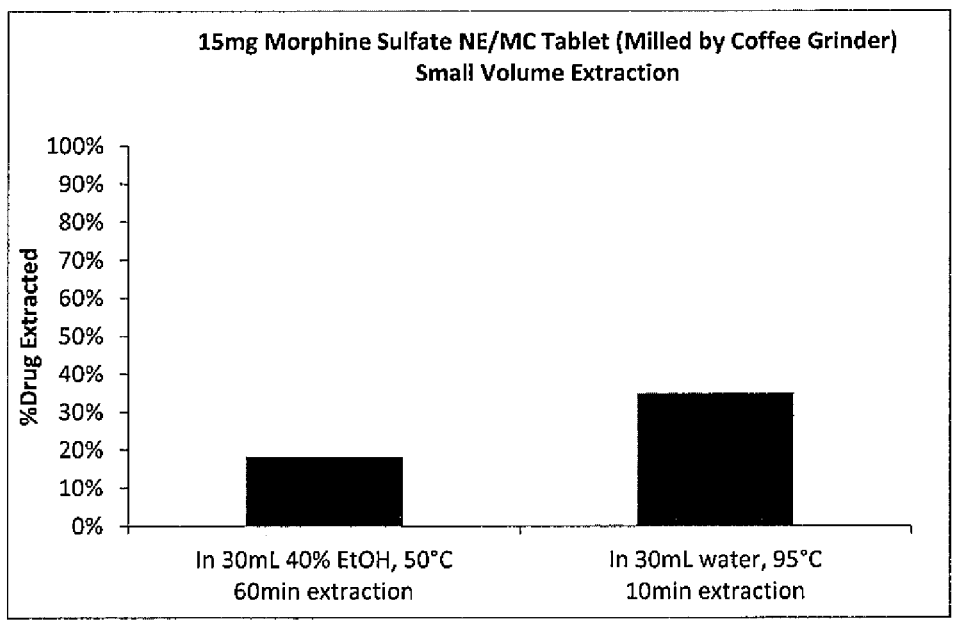
FIG. 18B is a graphical depiction of the small volume extraction data from Example 5A.

Example 5A 15 mg Morphine Sulfate NE/MC Tablet Small Volume Extraction & Syringability Studies Using the equipment and procedures referred to in Example 3, tablets according to Example 4A were tested for syringability and extractability by small volume of various solvents at various temperatures. The results are shown in FIG. 18A (water at room temperature and boiling) and 18B (40% ethanol at 50° C. and 95° C.).

Figure 19A:
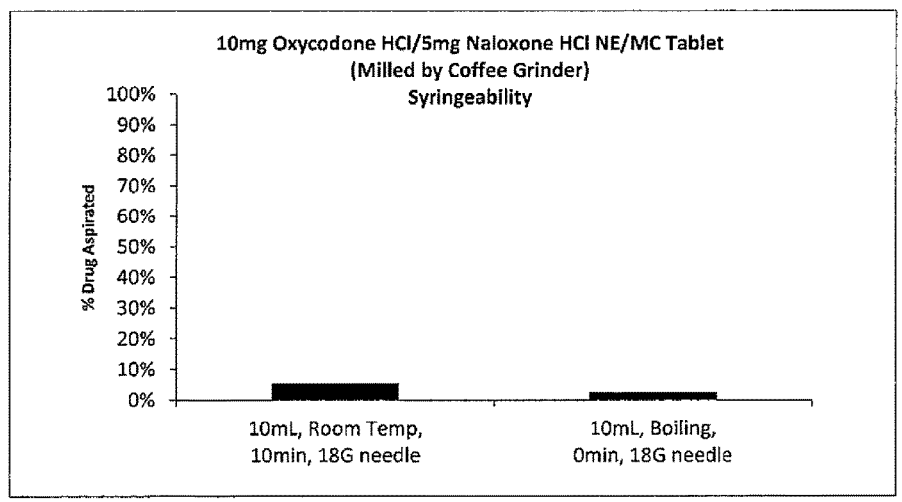
FIG. 19A is a graphical depiction of the syringability data from Example 5B.
Figure 19B:
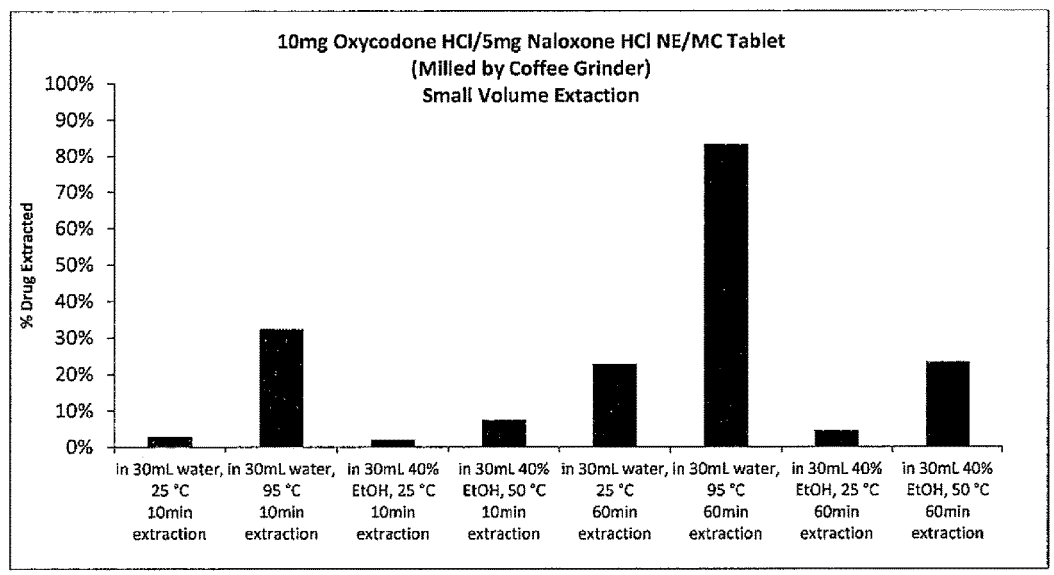
FIG. 19B is a graphical depiction of the small volume extraction data from Example 5B.

Example 5B 10 mg Oxycodone/5 mg Naloxone NE/MC Tablet Small Volume Extraction & Syringability Studies Using the equipment and procedures referred to in Example 3, tablets according to Example 4B were tested for syringability and extractability by small volume of various solvents at various temperatures. The results are shown in FIG. 19A (water at room temperature and boiling) and 19B (water and 40% ethanol at various temperatures).

Figure 20A:
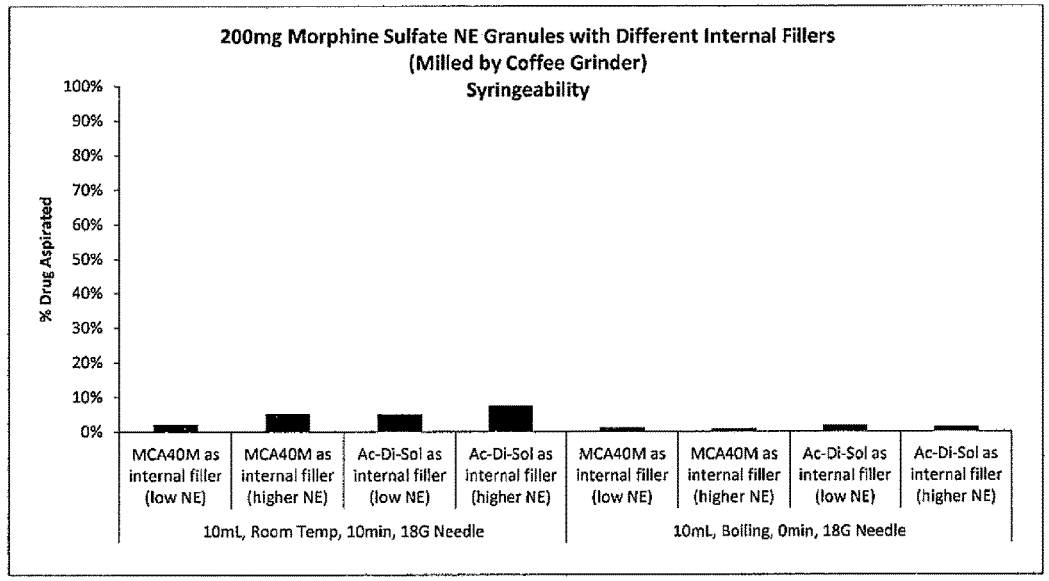
FIG. 20A is a graphical depiction of the syringability data from Example 5C.
Figure 20B:
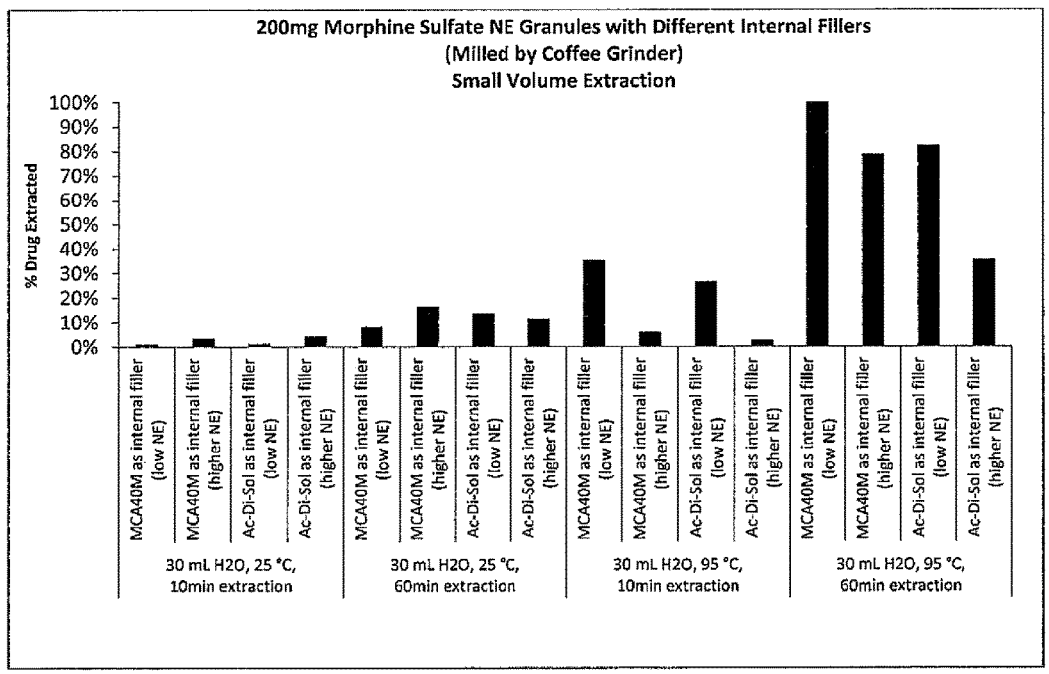
FIG. 20B is a graphical depiction of the small volume extraction data from Example 5C.

Example 5C 200 mg Morphine Sulfate NE Granulations with Different Internal Fillers Granules Small Volume Extraction & Syringability Studies Using the equipment and procedures referred to in Example 3, tablets according to Example 4C were tested for syringability and extractability by small volume of various solvents at various temperatures. The results are shown in FIG. 20A (water at room temperature and boiling) and 20B (water at 25 and 95° C.).

Example 6A

Preparation of 200 mg Morphine-Eudragit® NE Formulations using Different Pore Formers
Procedure:
Internal Core—Stage 1
  Equipment
  Vector GMX Micro High-Shear granulator
  Vector Fluid bed dryer
  Comil® Comminuting Mill
  Stainless Steel Screens—US Std. #18, #30
  Procedure
  1. A 4% w/w binder solution of Carbopol® 71G in 0.1 N HCl was prepared.
  2. Carbopol® 71G in the internal core was added in two parts. 50% of the Carbopol® 71G was added dry with morphine sulfate and methyl cellulose A40M (MCA40M) in the granulator. Remainder 50% Carbopol® 71G was added as the binder solution (from step 1).
  3. The ingredients for the internal core—morphine sulfate, methyl cellulose A40M (MC A40M) and Carbopol® 71G were charged into the bowl of high-shear granulator (impeller speed 300 rpm, chopper speed 300 rpm) and dry mixed for 1 minute.
  4. The mixture from step 3 was granulated with Carbopol® 71G binder solution (from step 1) which was sprayed at 40 g/min 5. If required, additional water was sprayed during granulation to obtain a cohesive free flowing mass.
6. The wet granulations were milled through Comil® fitted with mesh #18 (1000 micron opening) screen.
7. The wet milled granulations were dried in a fluid bed dryer at inlet temperature of 40° C., and an air volume adjusted to fluidize the bed. The moisture content of the dried granulations was <5%.
8. The dried granulations were milled through Comil® fitted with mesh #30 (600 micron opening) screen.

The composition (weight %) of the internal core is shown in Table 6A.1 below.

TABLE 6A.1

|  | Components | % (by weight) |
|---|---|---|
| Internal core | Morphine Sulfate | 46.5 |
|  | Carbopol ® 71G | 7.0 |
|  | MC A40M | 46.5 |

Eudragit® NE layer—Stage 2
Equipment: 100 mL food processor
Procedure:
Binder solutions were prepared by mixing Eudragit® NE dispersion and different pore formers, the compositions are shown in the Table 6A.2 below.

TABLE 6A.2

| Pore former | Eudragit ® NE solid concentration (%) | Pore Former concentration (%) |
|---|---|---|
| Lactose monohydrate | 38.8 | 2.91 |
| PEG 400 | 38.5 | 3.85 |
| PEG 4000 | 38.5 | 3.85 |
| Propylene glycol | 38.5 | 3.85 |
| NaCl | 37.0 | 7.41 |
| NaCl | 38.5 | 3.85 |
| HPMC E6 | 34.9 | 1.75 |
| Sodium CMC | 39.2 | 1.96 |
| SiO$_2$ | 39.2 | 1.96 |

1. The milled internal core granulations from Step 8/stage 1 were charged into the 100 mL food processor.
2. The binder solution was added slowly into the food processor to granulate the materials from step 1.
3. Wet granules from step 2 were dried in a vacuum oven at 60° C.
4. The dried granules from step 3 were recharged to the food processor; steps 2 and 3 were repeated until desired weight gain was reached.
5. The final coated granules were passed through sieve #30, and cured in a tray dryer at 60° C. for 24 hours.
6. Intact cured granules were tested for drug release in 900 mL Simulated Gastric Fluid (SGF) using the test method of Example 2.

Figure 21:
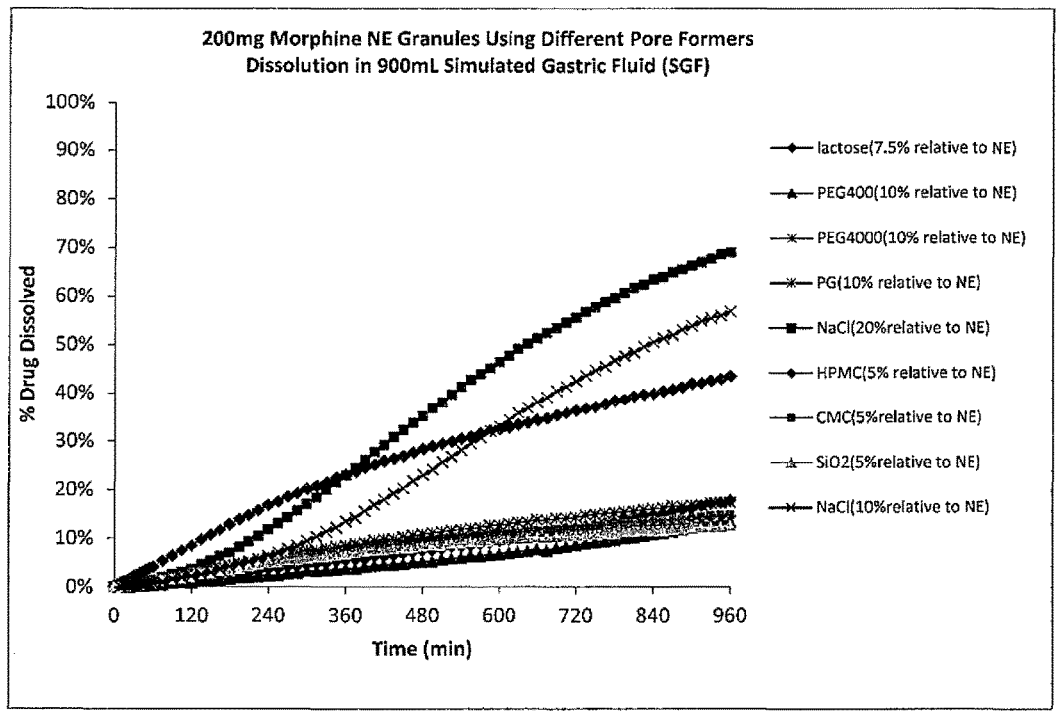
FIG. 21 is a graphical depiction of the dissolution of the formulation of Example 6A in SGF.

FIG. 21 shows the results of the dissolution tests of the formulations of Example 6A for each of the pore formers.

Example 6B

Preparation of 200 mg Morphine-Eudragit® NE Granule Formulations Using HPMC as a Pore Former The subject formulations were prepared with the compositions (weight %) of components as shown in Table 6B below, using the equipment and procedures referred to in Example 2 (excluding Stage 3).

TABLE 6B

|  | Components | Low NE % (by weight) | Intermediate NE % (by weight) | Higher NE % (by weight) |
|---|---|---|---|---|
| Internal core | Morphine Sulfate | 24.4 | 19.0 | 15.6 |
|  | Carbopol ® 71G | 24.4 | 19.0 | 15.6 |
|  | MC A40M | 5.5 | 4.3 | 3.5 |
| NE Layer | Eudragit ® NE | 43.5 | 55.0 | 62.3 |
|  | HPMC E6 | 2.2 | 2.7 | 3.1 |

Figure 22:
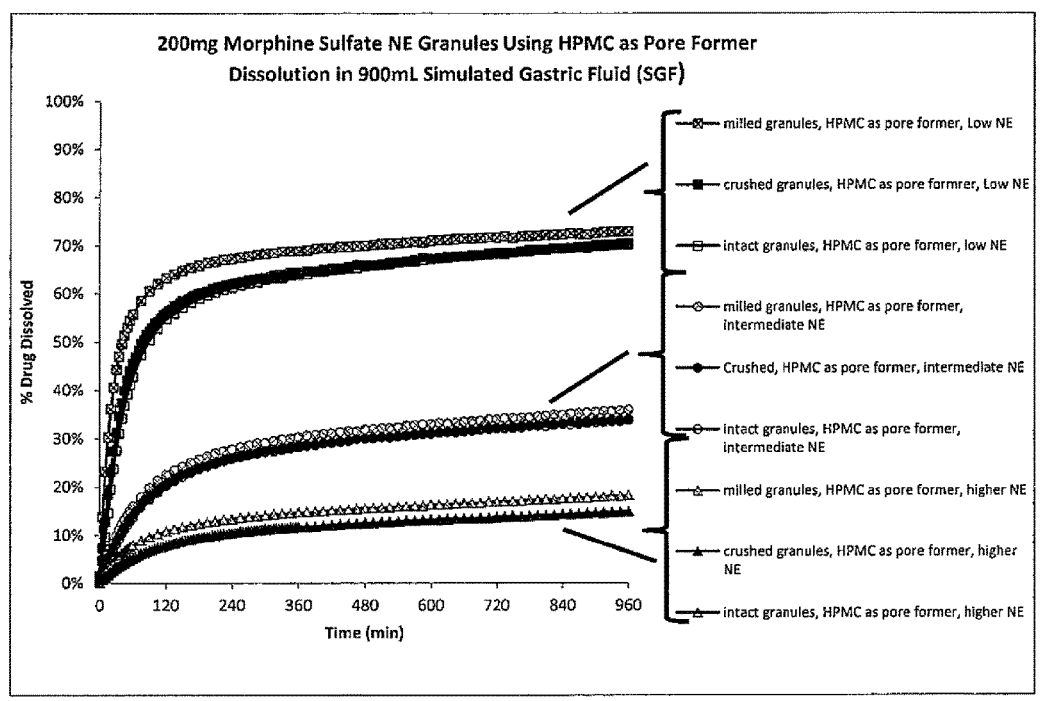
FIG. 22 is a graphical depiction of the dissolution of the formulation of Example 6B, milled, crushed or intact in SGF.

The granules of Example 6B were subject to milling, crushing and dissolution according to the protocols in Example 2. The dissolution of milled, crushed and intact final granules with low Eudragit® NE, milled, crushed and intact final granules with intermediate Eudragit® NE and milled, crushed and intact final granules with high Eudragit® NE in 900 mL SGF is shown in FIG. 22.

Example 6C

Preparation of 200 mg Morphine-Eudragit® NE Granule Formulations Using NaCl as a Pore Former The subject formulations were prepared with the compositions (weight %) of components as shown in Table 6C below, using the equipment and procedures referred to in Example 2 (excluding Stage 3).

TABLE 6C

|  | Components | Low NE % (by weight) | Intermediate NE % (by weight) | Higher NE % (by weight) |
|---|---|---|---|---|
| Internal core | Morphine Sulfate | 24.4 | 19.0 | 15.6 |
|  | Carbopol ® 71G | 24.4 | 19.0 | 15.6 |
|  | MC A40M | 5.5 | 4.3 | 3.5 |
| NE Layer | Eudragit ® NE | 43.5 | 55.0 | 62.3 |
|  | NaCl | 2.2 | 2.7 | 3.1 |

Figure 23:
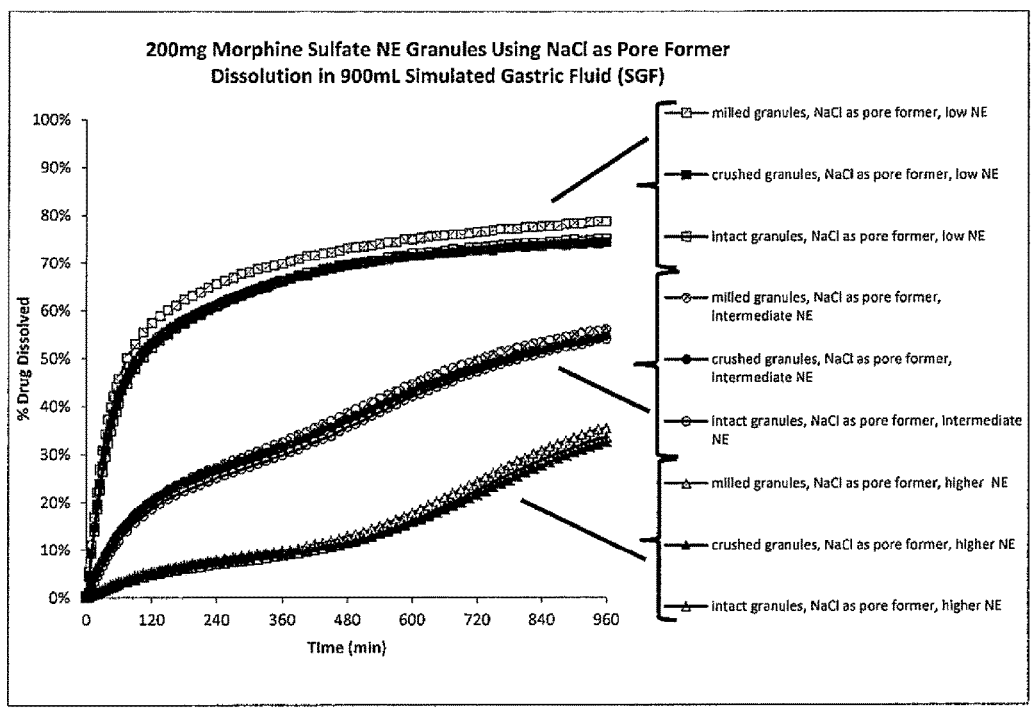
FIG. 23 is a graphical depiction of the dissolution of the formulation of Example 6C, milled, crushed or intact in SGF.

The granules of Example 6C were subject to milling, crushing and dissolution according to the protocols in Example 2. The dissolution of milled, crushed and intact final granules with low Eudragit® NE, milled, crushed and intact final granules with intermediate Eudragit® NE and milled, crushed and intact final granules with high Eudragit® NE in 900 mL SGF is shown in FIG. 23.

Example 6D

Figure 24A:
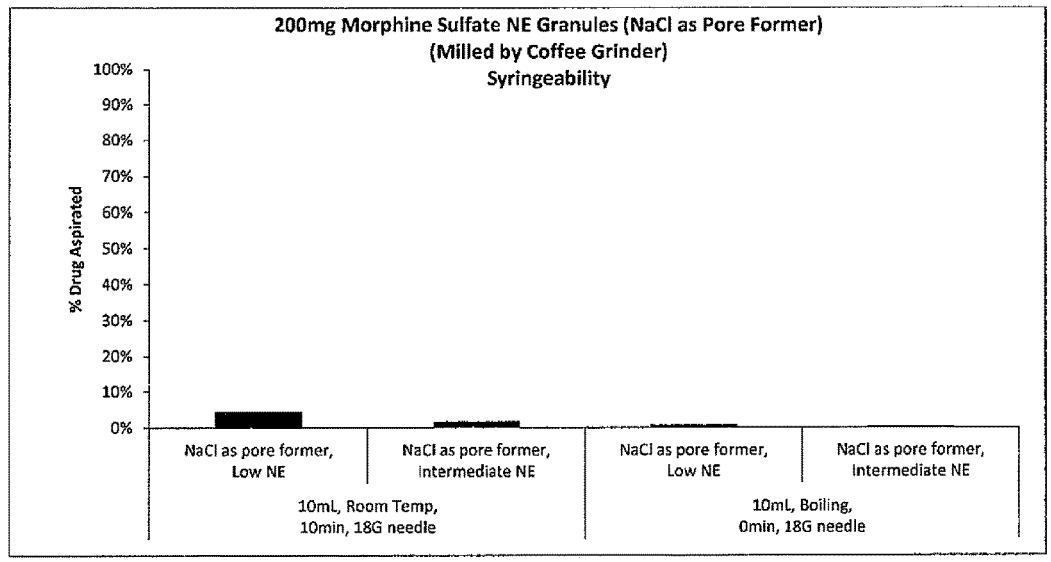
FIG. 24A is a graphical depiction of the syringability data from Example 6D.
Figure 24B:
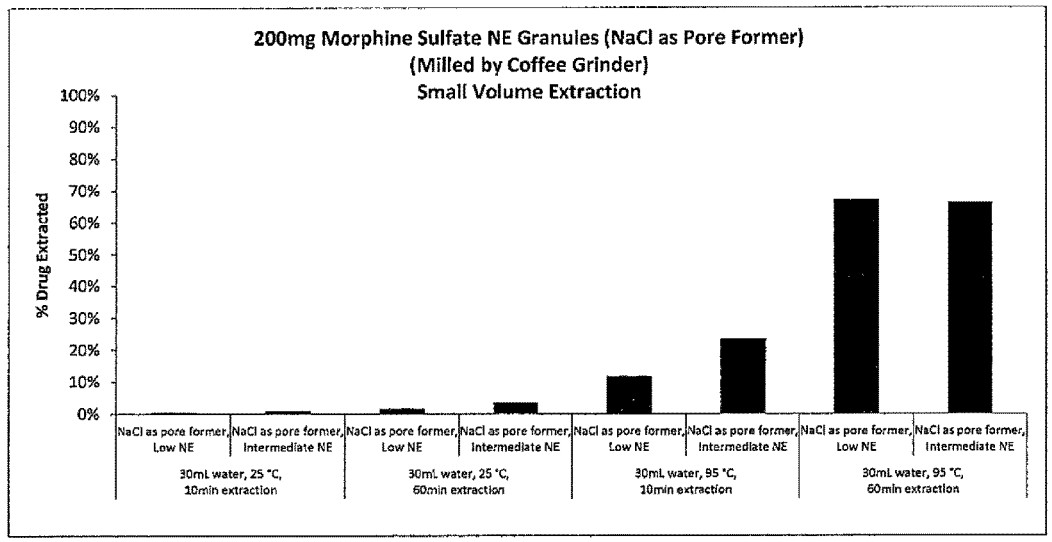
FIG. 24B is a graphical depiction of the small volume extraction data from Example 6D.

Small Volume Extraction & Syringability Studies of 200 mg Morphine NE Granule Formulations using NaCl as Pore Former Using the equipment and procedures referred to in Example 3, granules from Example 6D were tested for syringability and extractability by small volume of various solvents at various temperatures. The results are shown in FIG. 24A (water at room temperature and boiling) and 24B (water at various temperatures).

Example 7

15 mg Naloxone HCl.2H₂O—NE Core Granule Preparation

Core granule formulations were prepared as follows:

Internal Core—Stage 1

Equipment
10 L Collette High-Shear granulator
Vector VFC3 Fluid Bed Dryer
Comil® Comminuting Mill
Stainless Steel Screens—1016 μm, 813 μm, 595 μm
Procedure 1. A 4% w/w binder solution of Carbopol® 71G in 0.1 N HCl was prepared.
2. Carbopol® 71G in the internal core was added in two parts. 50%~70% of the Carbopol® 71G was added dry with Naloxone HCl.2H₂O and methyl cellulose (MCA40M) into the granulator. Remainder 30~50% of Carbopol® 71G was added as the binder solution (Step 1).
3. The ingredients of the internal core—naloxone HCl.2H₂O, methyl cellulose A40M (MC) and Carbopol® 71G (dry) were charged into the bowl of high-shear granulator (impeller speed 300 rpm, chopper speed 300 rpm) and dry mixed for 1 minute.
4. The mixture from step 3 was granulated with Carbopol® 71G solution which was sprayed at 60 g/min
5. If required additional water was sprayed during granulation to obtain a cohesive free flowing mass.
6. The wet granulations were milled through Comil® fitted with 1016 μm opening screen.
7. The wet milled granulations were dried in a fluid bed dryer at inlet temperature of 40° C., at an air volume adjusted to fluidize the bed. The moisture content of the dried granulation was <5%.
8. The dried granulations were first milled through Comil® fitted with 1016 μm opening screen, and then the materials larger than 595 μm were milled through Comil® fitted with 813 μm opening screen.

Eudragit® NE Layer—Stage 2

Equipment
Solidlab II
Stainless Steel Screen—US Std. #14
Hotpack Tray Dryer
Procedure 1. Binder solution was prepared by mixing Eudragit® NE 40D dispersion and lactose monohydrate (weight ratio of solid Eudragit® NE and lactose is 1/0.075) to obtain total solids content of 41.75% w/w in the dispersion.
2. After Solidlab II was preheated to around 25° C., the internal core granulation from Step 9/stage 1 was charged into the chamber of Solidlab II.
3. When the product temperature was 20° C., Eudragit® NE-lactose dispersion prepared in step 1/stage 2 was sprayed at spray rate=10-38 g/min, inlet airflow=150-300 m³/hr, inlet air temperature=20-40° C., product temperature=20° C., inlet air relative humidity=0%.
4. The product temperature was monitored and controlled by adjusting binder spray rate, inlet airflow, and inlet air temperature.
5. Granule samples were collected at various levels of Eudragit® NE loading for testing. When 440% weight gain was obtained, the coating was stopped.
6. After the collected granule samples were dried in the oven at 25° C., the granules were cured in a tray dryer at 60° C. for 24 hours.
7. The cured granules were de-agglomerated through #14 mesh screen.
8. Dissolution was tested on the milled and intact cured granules from step 7/stage2

The composition of the core granulations is shown in the Table 7 below.

TABLE 7

| | Components | % |
|---|---|---|
| Internal Core | Naloxone HCl•2H₂O | 9.6 |
| | Carbopol ® 71G | 2.4 |
| | MC A40M | 36.0 |
| NE Layer | Eudragit ® NE | 48.4 |
| | Lactose monohydrate | 3.6 |

Dissolution of the core granules was performed as follows:
1. Apparatus USP Type 2, paddles, 50 rpm at 37° C.
2. Media—900 ml simulated gastric fluid (SGF, pH 1.2)
3. Analytical method—UV analysis, Distek Fiber Optic Dissolution System (Distek Opt-Diss 405) at wavelength 280 nm, double wavelength correction.

Milling
1. One dose was added to the chamber of Krups coffee mill and milled for 15 sec, switching off for 10 sec. This procedure was repeated 3 more times for a total milling time of 60 sec.
2. Dissolution testing of milled samples in SGF was performed as described in "Dissolution" above.

Figure 25:
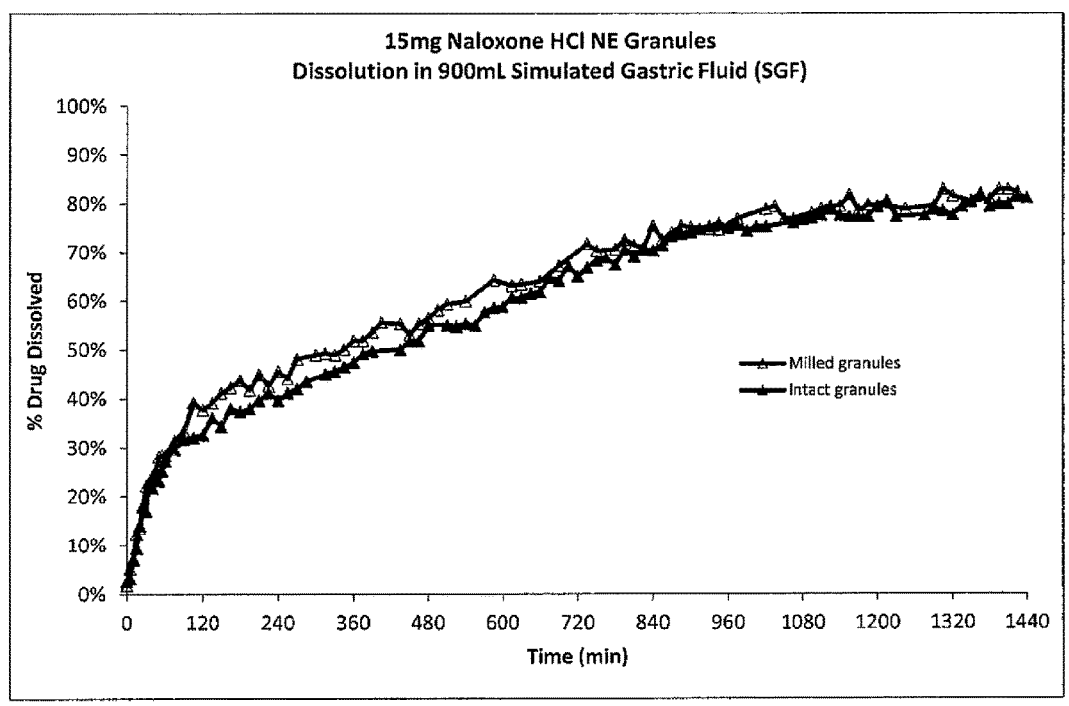
FIG. 25 is a graphical depiction of the dissolution in SGF of the formulation of Example 7 intact and milled.

The dissolution profiles of the intact and milled core granulations (NE (wt)/core (wt): 1.01) are shown in FIG. 25.

We claim:

1. A solid oral dosage form comprising a plurality of particles, each particle comprising:
   a core comprising an active agent susceptible to abuse;
   an internal adhesion promoter in an amount of about 0.05% (w/w) to about 10% (w/w) based on total weight of the dosage form; and
   an alcohol resistant material in an amount of about 1% (w/w) to about 50% (w/w) based on total weight of the dosage form;
   wherein the cores are (i) dispersed in a matrix comprising a controlled release material or (ii) coated with a controlled release material.

2. The solid oral dosage form of claim 1, wherein the core further comprises a dissolution enhancer in an amount of about 1% (w/w) to about 10% (w/w).

3. The solid oral dosage form of claim 1, wherein the coating or matrix further comprises a pore former in an amount of about 0.5% (w/w) to about 25% (w/w).

4. The solid oral dosage form of claim 1, further comprising an external adhesion promoter to promote the adhesion of the alcohol resistant material and the controlled release material in an amount of about 0.05% (w/w) to about 10% (w/w).

5. The solid oral dosage form of claim 1, wherein the controlled release material is a polymer.

6. The solid oral dosage form of claim 1, wherein the controlled release material is an acrylic polymer.

7. The solid oral dosage form of claim 1, wherein controlled release material is a neutral acrylic polymer.

8. The solid oral dosage form of claim 1, wherein the internal adhesion promoter is selected from the group consisting of a cellulosic material, a surfactant, a carbomer and a mixture thereof.

9. The solid oral dosage form of claim 8, wherein the cellulosic material is hydroxypropylmethyl cellulose.

10. The solid oral dosage form of claim 8, wherein the surfactant is a non-ionic surfactant.

11. The solid oral dosage form of claim 10, wherein the non-ionic surfactant is selected from the group consisting of a nonoxynol, a sorbitan ester and a mixture thereof.

12. The solid oral dosage form of claim 8, wherein the internal adhesion promoter is a carbomer.

13. The solid oral dosage form of claim 2, wherein the dissolution enhancer is a cellulosic material, a sugar, a starch or a polymer.

14. The solid oral dosage form of claim 2, wherein the dissolution enhancer is an alkylcellulose.

15. The solid oral dosage form of claim 2, wherein the dissolution enhancer is methylcellulose.

16. The solid oral dosage form of claim 3, wherein the pore former is a polysaccharide, a polymer, an organic solvent or an inorganic material.

17. The solid oral dosage form of claim 3, wherein the pore former is selected from the group consisting of sodium chloride, lactose, dextrose, mannitol, microcrystalline cellulose, methylcellulose and a mixture thereof.

18. The solid oral dosage form of claim 1, wherein the alcohol resistant material is a cellulosic material.

19. The solid oral dosage form of claim 1, wherein the alcohol resistant material is an alkylcellulose.

* * * * *

UNITED STATES PATENT AND TRADEMARK OFFICE
CERTIFICATE OF CORRECTION

Page 1 of 1

PATENT NO. : 10,517,832 B2
APPLICATION NO. : 16/234732
DATED : December 31, 2019
INVENTOR(S) : Rama Shmeis et al.

It is certified that error appears in the above-identified patent and that said Letters Patent is hereby corrected as shown below:

On the Title Page

After item (65) and before item (51), the following should be added:
--(62) Related U.S. Application Data
Continuation of application No. 15/484,777, filed on April 11, 2017, now Pat. No. 10,195,152, which is a Division of application No. 14/776,287, filed on September 14, 2015, now Pat. No. 9,616,030, which is a National Stage Entry of application No. PCT/US2014/028260, filed on March 14, 2014, which claims benefit of Provisional application No. 61/798,213, filed on March 15, 2013.--

Signed and Sealed this
Twenty-fifth Day of August, 2020

Andrei Iancu
*Director of the United States Patent and Trademark Office*